(12) United States Patent
Hu et al.

(10) Patent No.: US 11,222,447 B2
(45) Date of Patent: Jan. 11, 2022

(54) INTER-FRAME MOTION CORRECTION IN WHOLE-BODY DIRECT PARAMETRIC IMAGE RECONSTRUCTION

(71) Applicant: Siemens Medical Solutions USA, Inc., Malvern, PA (US)

(72) Inventors: Jicun Hu, Knoxville, TN (US); Ludovic Sibille, Knoxville, TN (US); Bruce Spottiswoode, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 149 days.

(21) Appl. No.: 15/929,496

(22) Filed: May 6, 2020

(65) Prior Publication Data

US 2021/0350591 A1    Nov. 11, 2021

(51) Int. Cl.
*G06T 11/00* (2006.01)
*A61B 6/00* (2006.01)
*A61B 6/03* (2006.01)

(52) U.S. Cl.
CPC ............ *G06T 11/005* (2013.01); *A61B 6/032* (2013.01); *A61B 6/037* (2013.01); *A61B 6/5264* (2013.01); *G06T 2210/41* (2013.01); *G06T 2211/424* (2013.01)

(58) Field of Classification Search
CPC .............. G06T 11/005; G06T 2210/41; G06T 2211/424; A61B 6/032; A61B 6/037; A61B 6/5264
See application file for complete search history.

(56) References Cited

U.S. PATENT DOCUMENTS

2011/0275933 A1* 11/2011 Dey .................... G01T 1/00
600/428

OTHER PUBLICATIONS

Jiao, Jieqing et al., "Direct Parametric Reconstruction with Joint Motion Estimation/Correction for Dynamic Brain PET Data", IEEE Transactions on Medical Imaging, pp. 203-212, vol. 36, 2017.
Chan, Chung et al., "Event-by-event respiratory motion ccorrection for PET with 3D internal-1D external motion correlation", Medical Physics 40, 112507 (2013); doi: 10.1118/1.4826165.

(Continued)

*Primary Examiner* — Courtney D Thomas

(57) ABSTRACT

A method for parametric image reconstruction and motion correction using whole-body motion fields includes receiving a nuclear imaging data set including a set of dynamic frames and generating at least one of a whole-body forward motion field and/or a whole-body inverse motion field for at least one frame in the set of frames. An iterative loop is applied to update at least one parameter used in a direct parametric reconstruction and at least one parametric image is generated based on the at least one parameter updated by the iterative loop. The iterative loop includes calculating a frame emission image for the at least one frame, generating a motion-corrected frame emission image based on the at least one whole-body forward motion field or a whole-body inverse motion field, and updating at least one parameter by applying a fit to the motion-corrected frame emission image.

20 Claims, 18 Drawing Sheets

(56) References Cited

OTHER PUBLICATIONS

Lu, Yihuan et al., "Data-driven voluntary body motion detection and non-rigid event-by-event correction for static and dynamic PET", Physics in Medicine and Biology, 2019, vol. 64, pp. 1-13.

Saddi, Kinda Anna et al.,"Region-based segmentation via non-rigid template matching", IEEE Int. Conference on Computer Vision, pp. 1-7, Oct. 2007.

Guetter, Christoph et al., "Efficient symmetric and inverse-consistent deformable registration through interleaved optimization," Proceedings of IEEE International Symposium on Biomedical Imaging: from nano to macro, Mar. 2011, DOI: 10.1109/ISBI.2011.5872476.

* cited by examiner

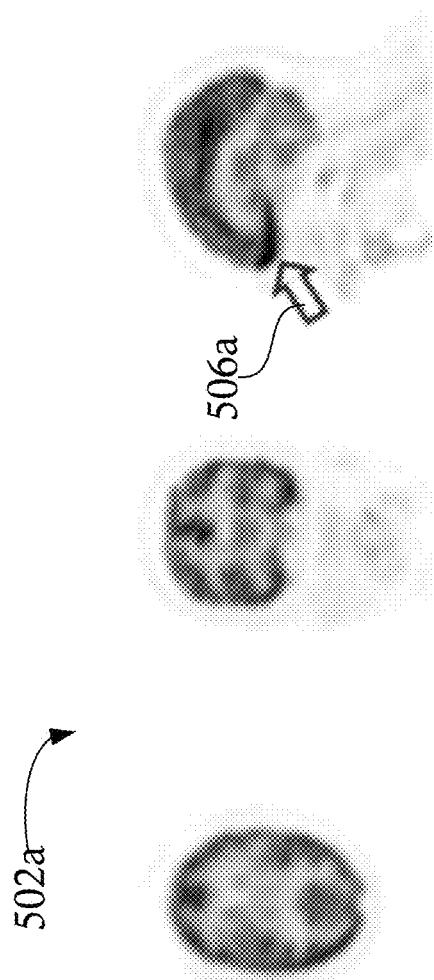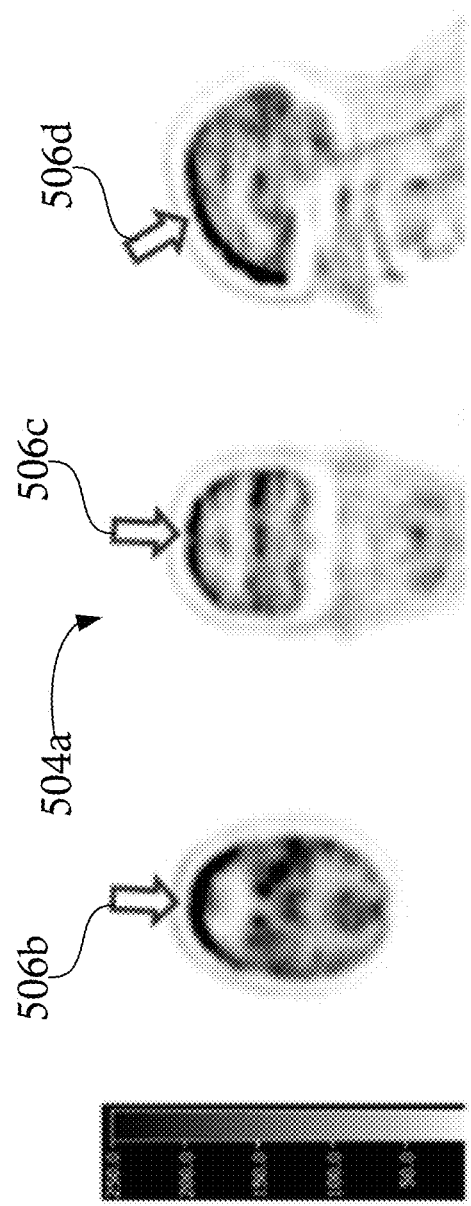
FIG. 9A
FIG. 9B

INTER-FRAME MOTION CORRECTION IN WHOLE-BODY DIRECT PARAMETRIC IMAGE RECONSTRUCTION

TECHNICAL FIELD

This application relates generally to nuclear imaging and, more particularly, to motion correction in nuclear imaging.

BACKGROUND

Current whole-body PET parametric imaging uses multiple passes or frames to acquire dynamic data so that activity change over time in each image voxel can be captured. To evaluate tracer kinetics accurately, ideally each voxel contains the same tissue for the duration of the scan. However, the dynamic data acquisition time span for each region of interest may be longer than the static standard uptake values (SUV) imaging and patients may move during a scan, resulting in motion artifacts in a reconstructed parametric image.

Typical motion includes head motion, respiratory motion, and bulk motion. In order to reduce motion artifacts, different dynamic frames need to be registered to the same reference frame with motion fields before the kinetics parameters are calculated.

SUMMARY

In various embodiments, a computer-implemented method is disclosed. The method includes receiving a nuclear imaging data set including a set of frames, generating at least one of a whole-body forward motion field or a whole-body inverse motion field for at least one frame in the set of frames, applying an iterative loop to update at least one parameter used in a direct parametric reconstruction, and generating at least one parametric image based on the at least one parameter updated by the iterative loop. The iterative loop includes calculating a frame emission image for the at least one frame, generating a motion-corrected frame emission image based on the at least one whole-body forward motion field or a whole-body inverse motion field, updating the at least one parameter by applying a linear fit to the motion-corrected frame emission image.

In various embodiments, a system is disclosed. The system includes a nuclear imaging scanner configured to obtain a set of nuclear imaging data including a set of dynamic frames and a processor. The processor is configured to receive the nuclear imaging data set from the nuclear imaging scanner, generate at least one of a whole-body forward motion field or a whole-body inverse motion field for at least one frame in the set of frames, apply an iterative loop to update at least one parameter used in a direct parametric reconstruction, and generate at least one parametric image based on the at least one parameter updated by the iterative loop. The iterative loop includes calculating a frame emission image for the at least one frame, generating a motion-corrected frame emission image based on the at least one whole-body forward motion field or a whole-body inverse motion field, and updating the at least one parameter by applying a linear fit to the motion-corrected frame emission image.

In various embodiments, a non-transitory computer readable medium storing instructions configured to cause a computer system to execute steps including receiving a nuclear imaging data set including a set of frames, generating at least one of a whole-body forward motion field or a whole-body inverse motion field for at least one frame in the set of frames, applying an iterative loop to update at least one parameter used in a direct parametric reconstruction, and generating at least one parametric image based on the at least one parameter updated by the iterative loop. The iterative loop includes calculating a frame emission image for the at least one frame, generating a motion-corrected frame emission image based on the at least one whole-body forward motion field or a whole-body inverse motion field, updating at least one parameter by applying a linear fit to the motion-corrected frame emission image.

BRIEF DESCRIPTION OF THE DRAWINGS

The features and advantages of the present invention will be more fully disclosed in, or rendered obvious by the following detailed description of the preferred embodiments, which are to be considered together with the accompanying drawings wherein like numbers refer to like parts and further wherein:

FIG. 9A illustrates a metabolic uptake rate (Ki) brain parametric image reconstructed without applying motion correction.

FIG. 9B illustrates distribution volume (DV) brain parametric image reconstructed without applying motion correction.

DETAILED DESCRIPTION

Figure 1:
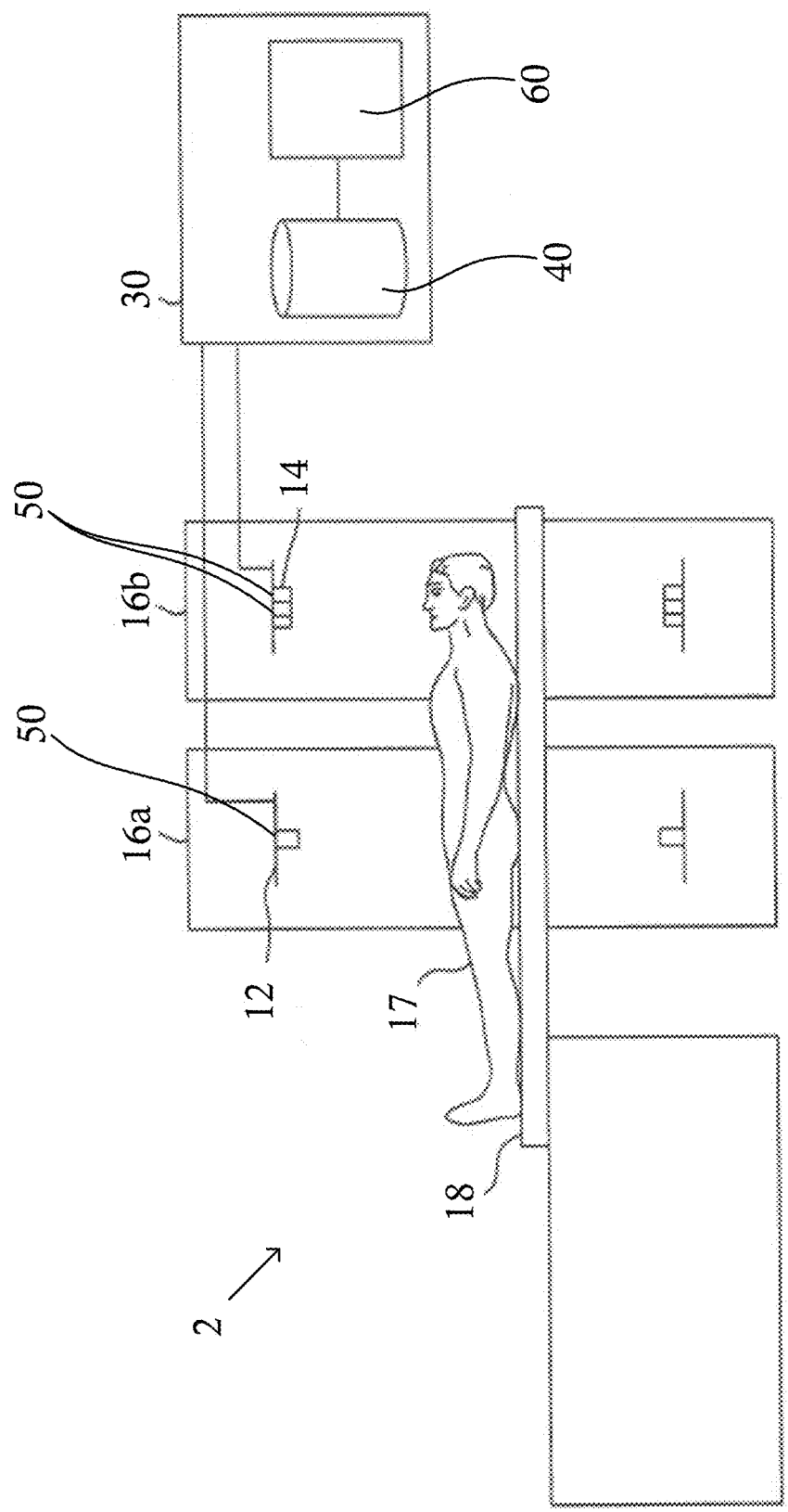
FIG. 1 illustrates a nuclear imaging system, in accordance with some embodiments.

The description of the exemplary embodiments is intended to be read in connection with the accompanying drawings, which are to be considered part of the entire written description. In the description, relative terms should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are operatively connected or attached to one another either directly or indirectly through intervening structures, including physical, electrical, optical, or other attachments or relationships, unless expressly described otherwise.

In various embodiments, a whole-body motion field calculated from deformable registration is used in a direct parametric reconstruction to calculate one or more parameters for generating parametric diagnostic images. Forward and inverse motion fields are calculated based on a reference frame for each frame in a set of frames. During a direct parametric reconstruction, the forward and inverse motion fields for each frame are used to generate iterative correction images applied to emission images for each frame to update one or more parameters used in the parametric reconstruction. One or more parametric images are generated for diagnostic and/or clinical purposes.

FIG. 1 illustrates one embodiment of a nuclear imaging system 2. The nuclear imaging system 2 includes at least a first imaging modality 12 provided in a first gantry 16a. The first imaging modality 12 may include any suitable modality, such as, for example, a computed-tomography (CT) modality, a positron-emission tomography (PET) modality, a single-photon emission computerized tomography (SPECT) modality, etc. The first imaging modality 12 can include a long axial field-of-view (FOV) or a short axial FOV. A patient 17 lies on a movable patient bed 18 that may be movable with respect to the first gantry 16a. In some embodiments, the nuclear imaging system 2 includes a second imaging modality 14 provided in a second gantry 16b. The second imaging modality 14 can be any suitable imaging modality, such as, for example, a CT modality, a PET modality, a SPECT modality and/or any other suitable imaging modality. The second modality 14 may include a long axial FOV or a short axial FOV. Each of the first imaging modality 12 and/or the second imaging modality 14 can include one or more detectors 50 arranged, for example, in one or more rings. Each of the detectors 50 is configured to detect an annihilation photon, gamma ray, and/or other nuclear imaging event.

Scan data from the first imaging modality 12 and/or the second imaging modality 14 is stored at one or more computer databases 40 and processed by one or more computer processors 60 of a computer system 30. The graphical depiction of computer system 30 in FIG. 1 is provided by way of illustration only, and computer system 30 may include one or more separate computing devices, for example, as described with respect to FIG. 2. The scan data may be provided by the first imaging modality 12, the second imaging modality 14, and/or may be provided as a separate data set, such as, for example, from a memory coupled to the computer system 30. The computer system 30 can include one or more processing electronics for processing a signal received from one of the plurality of detectors 50.

Figure 2:
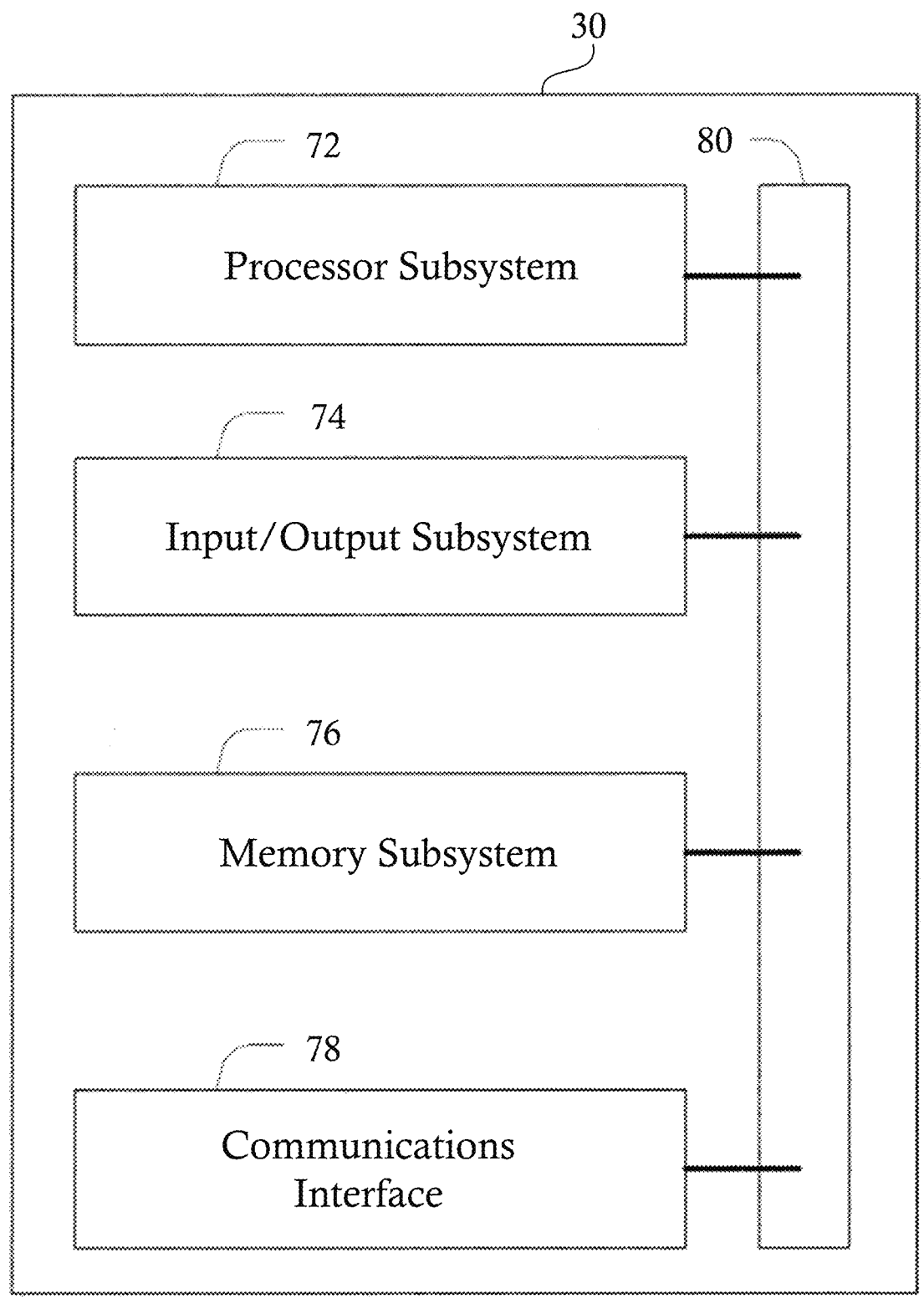
FIG. 2 illustrates a block diagram of a computer system, in accordance with some embodiments.

FIG. 2 illustrates a computer system 30 configured to implement one or more processes, in accordance with some embodiments. The system 30 is a representative device and can include a processor subsystem 72, an input/output subsystem 74, a memory subsystem 76, a communications interface 78, and a system bus 80. In some embodiments, one or more than one of the system 30 components can be combined or omitted such as, for example, not including an input/output subsystem 74. In some embodiments, the system 30 can comprise other components not shown in FIG. 2. For example, the system 30 can also include, for example, a power subsystem. In other embodiments, the system 30 can include several instances of a component shown in FIG. 2. For example, the system 30 can include multiple memory subsystems 76. For the sake of conciseness and clarity, and not limitation, one of each component is shown in FIG. 2.

The processor subsystem 72 can include any processing circuitry operative to control the operations and performance of the system 30. In various aspects, the processor subsystem 72 can be implemented as a general purpose processor, a chip multiprocessor (CMP), a dedicated processor, an embedded processor, a digital signal processor (DSP), a network processor, an input/output (I/O) processor, a media access control (MAC) processor, a radio baseband processor, a co-processor, a microprocessor such as a complex instruction set computer (CISC) microprocessor, a reduced instruction set computing (RISC) microprocessor, and/or a very long instruction word (VLIW) microprocessor, or other processing device. The processor subsystem 72 also can be implemented by a controller, a microcontroller, an application specific integrated circuit (ASIC), a field programmable gate array (FPGA), a programmable logic device (PLD), and so forth.

In various aspects, the processor subsystem 72 can be arranged to run an operating system (OS) and various applications. Examples of an OS comprise, for example, operating systems generally known under the trade name of Apple OS, Microsoft Windows OS, Android OS, Linux OS, and any other proprietary or open source OS. Examples of applications comprise, for example, network applications, local applications, data input/output applications, user interaction applications, etc.

In some embodiments, the system 30 can include a system bus 80 that couples various system components including the processing subsystem 72, the input/output subsystem 74, and the memory subsystem 76. The system bus 80 can be any of several types of bus structure(s) including a memory bus or memory controller, a peripheral bus or external bus, and/or a local bus using any variety of available bus architectures including, but not limited to, 9-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect Card International Association Bus (PCM-CIA), Small Computers Interface (SCSI) or other proprietary bus, or any custom bus suitable for computing device applications.

In some embodiments, the input/output subsystem 74 can include any suitable mechanism or component to enable a user to provide input to system 30 and the system 30 to provide output to the user. For example, the input/output subsystem 74 can include any suitable input mechanism, including but not limited to, a button, keypad, keyboard, click wheel, touch screen, motion sensor, microphone, camera, etc.

In some embodiments, the input/output subsystem 74 can include a visual peripheral output device for providing a display visible to the user. For example, the visual peripheral output device can include a screen such as, for example, a Liquid Crystal Display (LCD) screen. As another example, the visual peripheral output device can include a movable display or projecting system for providing a display of content on a surface remote from the system 30. In some embodiments, the visual peripheral output device can include a coder/decoder, also known as Codecs, to convert digital media data into analog signals. For example, the visual peripheral output device can include video Codecs, audio Codecs, or any other suitable type of Codec.

The visual peripheral output device can include display drivers, circuitry for driving display drivers, or both. The visual peripheral output device can be operative to display content under the direction of the processor subsystem 72. For example, the visual peripheral output device can be able to play media playback information, application screens for application implemented on the system 30, information regarding ongoing communications operations, information regarding incoming communications requests, or device operation screens, to name only a few.

In some embodiments, the communications interface 78 can include any suitable hardware, software, or combination of hardware and software that is capable of coupling the system 30 to one or more networks and/or additional devices. The communications interface 78 can be arranged to operate with any suitable technique for controlling information signals using a desired set of communications protocols, services or operating procedures. The communications interface 78 can include the appropriate physical connectors to connect with a corresponding communications medium, whether wired or wireless.

Vehicles of communication comprise a network. In various aspects, the network can include local area networks (LAN) as well as wide area networks (WAN) including without limitation Internet, wired channels, wireless channels, communication devices including telephones, computers, wire, radio, optical or other electromagnetic channels, and combinations thereof, including other devices and/or components capable of/associated with communicating data. For example, the communication environments comprise in-body communications, various devices, and various modes of communications such as wireless communications, wired communications, and combinations of the same.

Wireless communication modes comprise any mode of communication between points (e.g., nodes) that utilize, at least in part, wireless technology including various protocols and combinations of protocols associated with wireless transmission, data, and devices. The points comprise, for example, wireless devices such as wireless headsets, audio and multimedia devices and equipment, such as audio players and multimedia players, telephones, including mobile telephones and cordless telephones, and computers and computer-related devices and components, such as printers, network-connected machinery, and/or any other suitable device or third-party device.

Wired communication modes comprise any mode of communication between points that utilize wired technology including various protocols and combinations of protocols associated with wired transmission, data, and devices. The points comprise, for example, devices such as audio and multimedia devices and equipment, such as audio players and multimedia players, telephones, including mobile telephones and cordless telephones, and computers and computer-related devices and components, such as printers, network-connected machinery, and/or any other suitable device or third-party device. In various implementations, the wired communication modules can communicate in accordance with a number of wired protocols. Examples of wired protocols can include Universal Serial Bus (USB) communication, RS-232, RS-422, RS-423, RS-485 serial protocols, FireWire, Ethernet, Fibre Channel, MIDI, ATA, Serial ATA, PCI Express, T-1 (and variants), Industry Standard Architecture (ISA) parallel communication, Small Computer System Interface (SCSI) communication, or Peripheral Component Interconnect (PCI) communication, to name only a few examples.

Accordingly, in various aspects, the communications interface 78 can include one or more interfaces such as, for example, a wireless communications interface, a wired communications interface, a network interface, a transmit interface, a receive interface, a media interface, a system interface, a component interface, a switching interface, a chip interface, a controller, and so forth. When implemented by a wireless device or within wireless system, for example, the communications interface 78 can include a wireless interface comprising one or more antennas, transmitters, receivers, transceivers, amplifiers, filters, control logic, and so forth.

In various aspects, the communications interface 78 can provide data communications functionality in accordance with a number of protocols. Examples of protocols can include various wireless local area network (WLAN) protocols, including the Institute of Electrical and Electronics Engineers (IEEE) 802.xx series of protocols, such as IEEE 802.11a/b/g/n/ac, IEEE 802.16, IEEE 802.20, and so forth. Other examples of wireless protocols can include various wireless wide area network (WWAN) protocols, such as GSM cellular radiotelephone system protocols with GPRS, CDMA cellular radiotelephone communication systems with 1xRTT, EDGE systems, EV-DO systems, EV-DV systems, HSDPA systems, and so forth. Further examples of wireless protocols can include wireless personal area network (PAN) protocols, such as an Infrared protocol, a protocol from the Bluetooth Special Interest Group (SIG) series of protocols (e.g., Bluetooth Specification versions 5.0, 6, 7, legacy Bluetooth protocols, etc.) as well as one or more Bluetooth Profiles, and so forth. Yet another example of wireless protocols can include near-field communication techniques and protocols, such as electro-magnetic induction (EMI) techniques. An example of EMI techniques can include passive or active radio-frequency identification (RFID) protocols and devices. Other suitable protocols can include Ultra Wide Band (UWB), Digital Office (DO), Digital Home, Trusted Platform Module (TPM), ZigBee, and so forth.

In some embodiments, at least one non-transitory computer-readable storage medium is provided having computer-executable instructions embodied thereon, wherein, when executed by at least one processor, the computer-executable instructions cause the at least one processor to perform embodiments of the methods described herein. This computer-readable storage medium can be embodied in memory subsystem 76.

In some embodiments, the memory subsystem 76 can include any machine-readable or computer-readable media capable of storing data, including both volatile/non-volatile memory and removable/non-removable memory. The memory subsystem 76 can include at least one non-volatile memory unit. The non-volatile memory unit is capable of storing one or more software programs. The software programs can contain, for example, applications, user data, device data, and/or configuration data, or combinations therefore, to name only a few. The software programs can contain instructions executable by the various components of the system 30.

In various aspects, the memory subsystem 76 can include any machine-readable or computer-readable media capable of storing data, including both volatile/non-volatile memory and removable/non-removable memory. For example, memory can include read-only memory (ROM), random-access memory (RAM), dynamic RAM (DRAM), Double-Data-Rate DRAM (DDR-RAM), synchronous DRAM (SDRAM), static RAM (SRAM), programmable ROM (PROM), erasable programmable ROM (EPROM), electrically erasable programmable ROM (EEPROM), flash memory (e.g., NOR or NAND flash memory), content addressable memory (CAM), polymer memory (e.g., ferroelectric polymer memory), phase-change memory (e.g., ovonic memory), ferroelectric memory, silicon-oxide-nitride-oxide-silicon (SONOS) memory, disk memory (e.g., floppy disk, hard drive, optical disk, magnetic disk), or card (e.g., magnetic card, optical card), or any other type of media suitable for storing information.

In one embodiment, the memory subsystem 76 can contain an instruction set, in the form of a file for executing various methods, such as methods including A/B testing and cache optimization, as described herein. The instruction set can be stored in any acceptable form of machine readable instructions, including source code or various appropriate programming languages. Some examples of programming languages that can be used to store the instruction set comprise, but are not limited to: Java, C, C++, C#, Python, Objective-C, Visual Basic, or .NET programming In some embodiments a compiler or interpreter is comprised to convert the instruction set into machine executable code for execution by the processing subsystem 72.

Figure 3A:
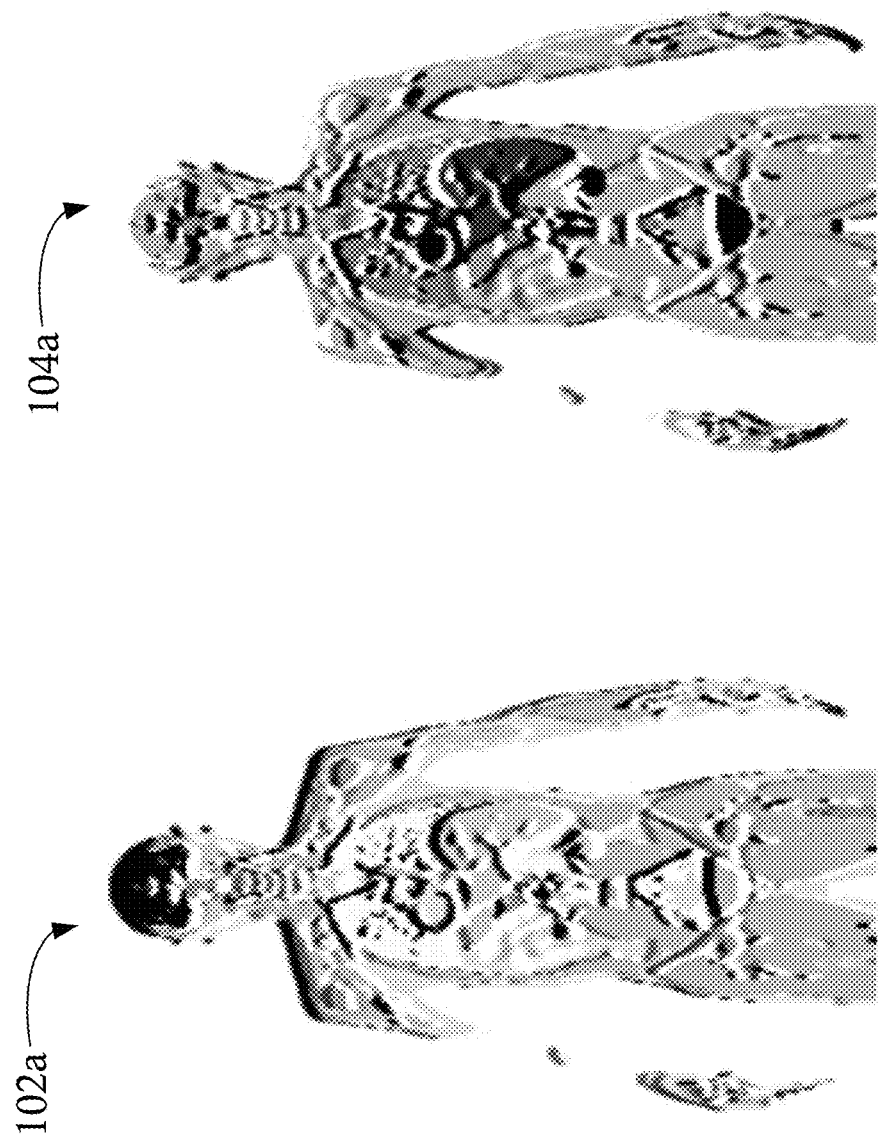
FIG. 3A illustrates reconstructed parametric images containing motion artifacts.
Figure 3B:
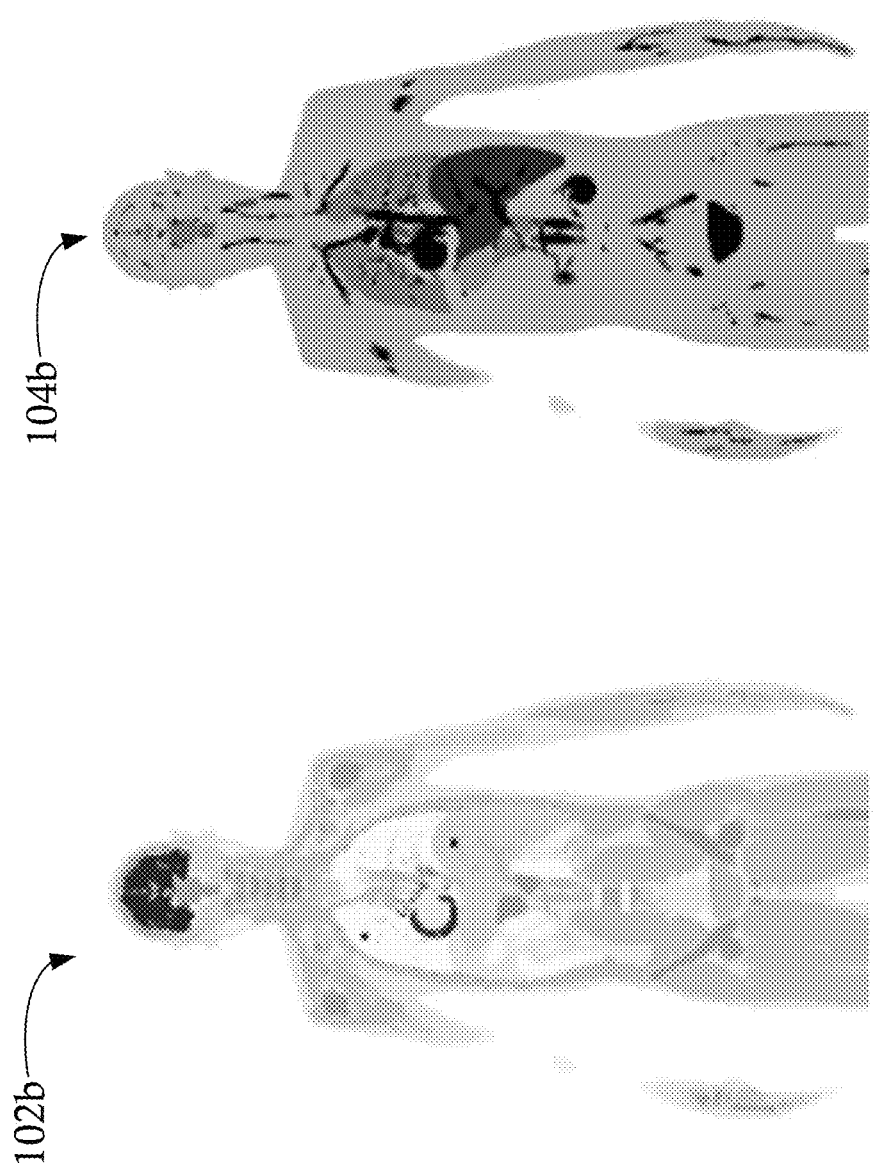
FIG. 3B illustrates ground-truth parametric images.

FIG. 3A illustrates reconstructed parametric images 102a, 104a generated from a simulated PET imaging data set that include motion artifacts and FIG. 3B illustrates their respective ground-truth parametric images 102b, 104b. As can be seen in FIGS. 3A and 3B, motion artifacts introduce significant distortions into images such that the reconstructed parametric images 102a, 104a do not have sufficient clinical value for diagnosis or treatment planning purposes. The significant artifacts in the reconstructed parametric images 102a, 104a as compared to the ground-truth parametric images 102b, 104b are caused by minor, rigid translational movements along axial direction between motion-free dynamic frames. In some embodiments, in order to avoid significant motion artifacts, motion correction can be applied using a whole-body motion field to correct for motion during parametric image reconstruction and eliminate motion artifacts.

Figure 4:
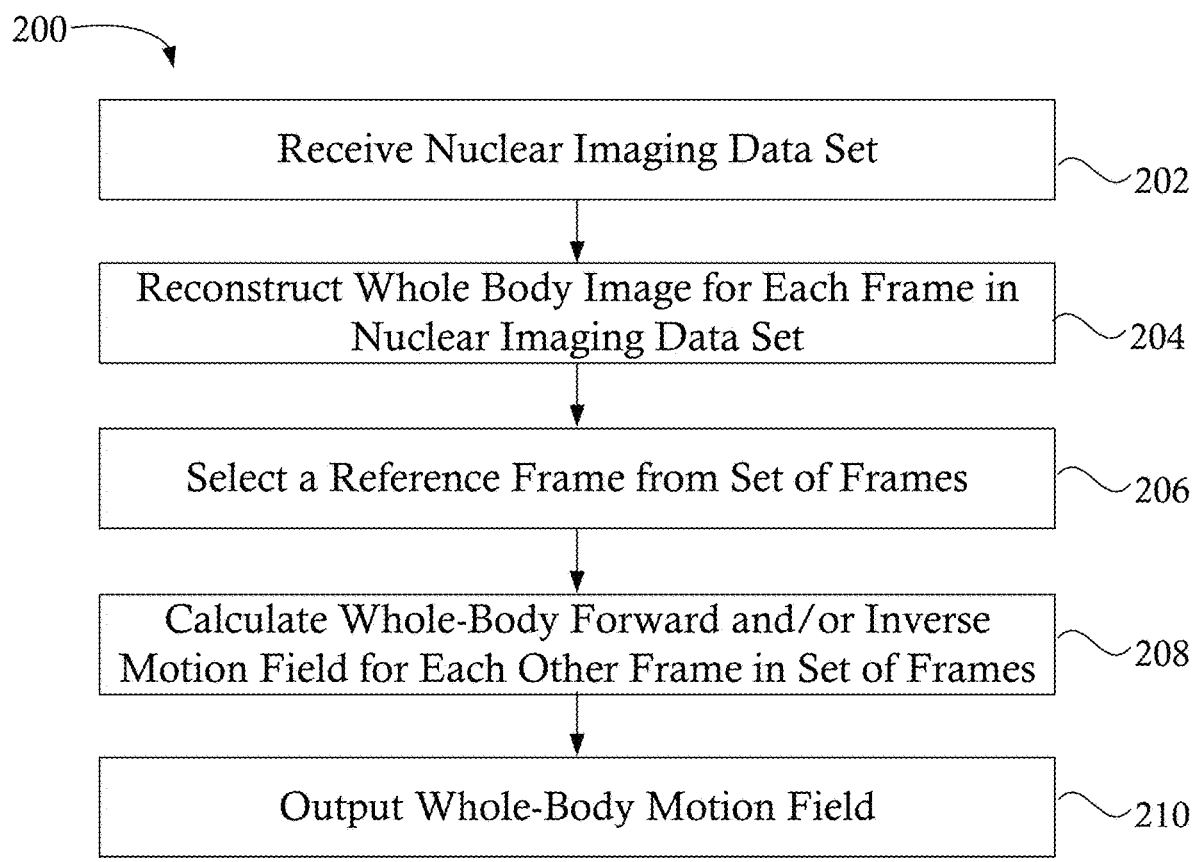
FIG. 4 is a flowchart illustrating a process of calculating a multi-frame motion field, in accordance with some embodiments.

FIG. 4 is a flowchart 200 illustrating a process of calculating a multi-frame motion field, in accordance with some embodiments. At step 202, a set of nuclear imaging data is received. The set of nuclear imaging data may include any suitable nuclear imaging data, such as, for example, listmode nuclear imaging data generated by one or more imaging modalities 12, 14. The listmode nuclear imaging data may include a set of frames and may include continuous-bed motion (CBM) sinograms, multi-bed sinograms, or single-bed sinograms. At step 204, a whole-body image is reconstructed for each frame in the set of nuclear imaging data to generate a set of reconstructed frame images. In some embodiments, a whole-body image may be generated using multi-bed or multi-chunk reconstruction and whole body stitching for limited FOV scanners. Any suitable multi-bed or multi-chunk reconstruction may be used to generate whole-body images for each frame. In some embodiments, single-bed whole-body images may be reconstructed for long FOV scanners (e.g., scanner longer than 1 meter).

At step 206, a reference frame is selected from the set of reconstructed frame images. A reference frame may be selected based on one or more criteria, such as, for example, selecting the first reconstructed frame image in the set of reconstructed frame images, the last reconstructed frame image in the set of reconstructed frame images, the reconstructed frame image having the smallest distance (i.e., least difference) with each of the other reconstructed frame images in the set, the reconstructed frame images most representative of the position of a patient, the reconstructed frame image being best aligned with CT data, and/or any other suitable criteria. Although various criteria are disclosed herein, it will be appreciated that any suitable criteria or combination of criteria may be used to select a reference frame.

At step 208, a forward whole-body motion field and an inverse (or reverse) whole-body motion field are calculated for each reconstructed frame image in the set with respect to the selected reference frame. For example, in embodiments having X reconstructed frame images, a reference frame, $X_R$, may be selected and a forward whole-body motion field and an inverse whole-body motion field may be calculated for each of the remaining X−1 reconstructed frame images with respect to the reference frame $X_R$. In some embodiments, forward and inverse motion fields are also calculated for the reference frame $X_R$, but it will be appreciated that such frames would be equal to zero (i.e., no difference).

A forward motion field includes a spatial mapping from each voxel position in a source image (i.e., each voxel image in a selected reconstructed frame image) to the voxel position in the reference frame. Similarly, an inverse motion field includes a spatial mapping from each voxel position in the reference frame to each voxel position in the source image. In some embodiments, the forward motion field and inverse motion field for each reconstructed frame image may be calculated independently. In some embodiments, a first one of the forward motion field or the inverse motion field may be calculated and a second one of the forward motion field or the inverse motion field derived from the calculated motion field, for example, by applying in inverse function.

Figure 8:
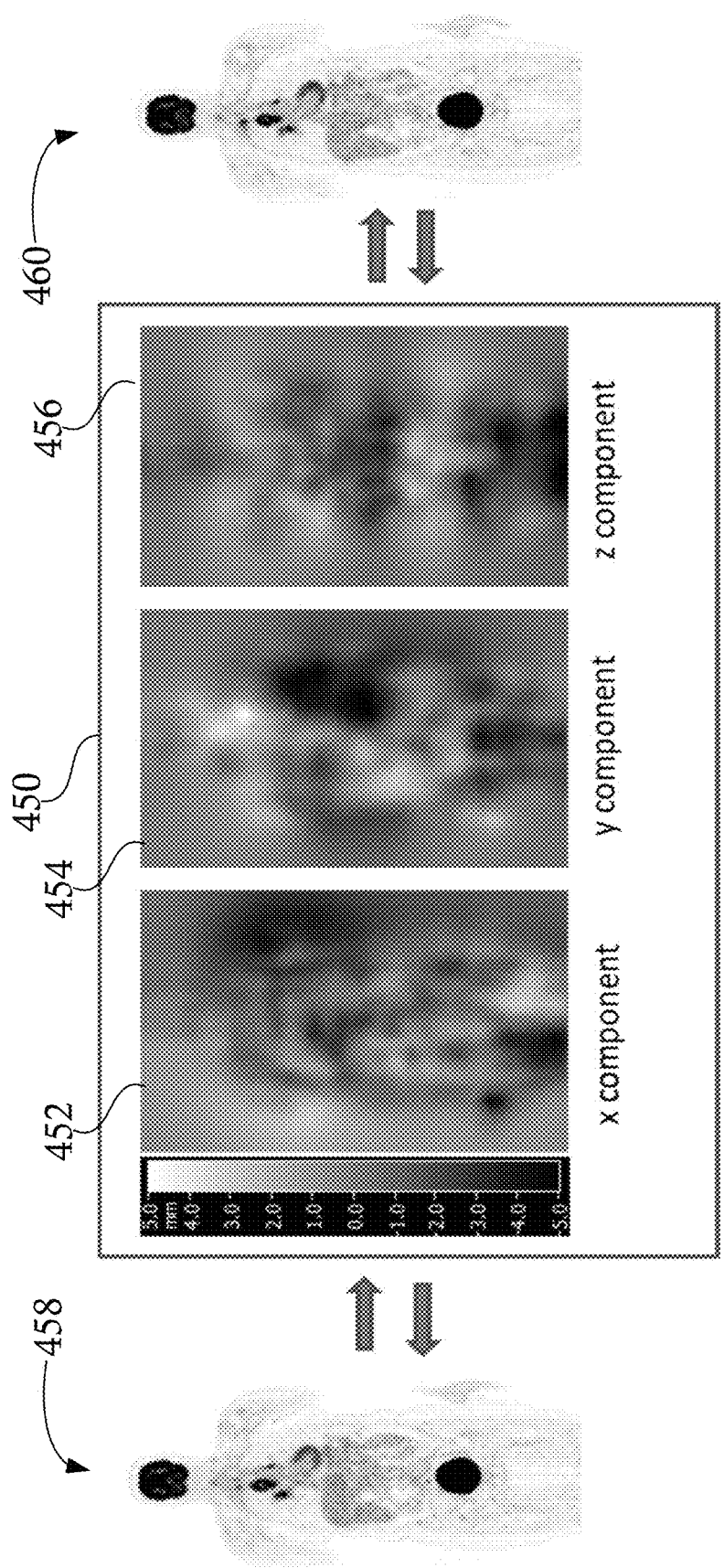
FIG. 8 illustrates applying a whole-body motion field to warp an image frame to a reference frame, in accordance with some embodiments.

In some embodiments, each of the forward whole-body motion field and the inverse whole-body motion field include an x component, a y component, and a z component. One embodiment of a motion field 450 is illustrated in FIG. 8, as discussed in greater detail below. The forward and/or inverse whole-body motion fields may be generated using any suitable process. For example, in some embodiments, the forward and/or inverse whole-body motion fields may be calculated based on registration algorithms applied in an image space. Calculating the whole-body parametric images with motion correction requires two rounds of reconstructions, a first set of image reconstructions (generated at step 202) used to determine whole-body motion fields and a second set of image reconstructions (as discussed with respect to FIG. 5) for use in diagnostic and clinical determinations of kinetics parameters. In some embodiments, a smoothing constraint may be applied such that a fully iterative reconstruction of each reconstructed frame image is not necessary to derive forward and/or inverse motion fields. Using a smoothing constraint may also allow for motion correction at a higher temporal resolution, allowing body motion to be captured with higher accuracy.

As another example, in some embodiments, the computational requirements of steps 202-206 may be reduced by applying direct histogramming to generate histo-images for use in calculation of the forward and/or inverse whole-body motion fields in near real-time. A histo-image is an image reconstructed directly from list mode data by assigning each detected count to a voxel in an image using time of flight information. Although such images are not suitable for diagnostic purposes, they are suitable for registration. An artificial intelligence (AI) filtering process (e.g., trained network using fully reconstructed images as a reference) may be applied to improve the quality of the histo-images, improving registration of each frame to a reference frame in the list mode data.

In some embodiments, one or more trained AI networks, such as a trained neural network, may be applied to improve quality of generated histo-images. For example, in some embodiments, one or more supervised learning processes may be applied to train a neural network to filter and improve quality of histo-images generated based on direct histogramming. The trained network may be trained based on a fully reconstructed image (e.g., a ground-truth image). In some embodiments, the neural network is trained to understand kinetics applicable to the histo-images to produce images that have similar contrast to improve calculation of motion fields based on the histo-images. Although specific embodiments are discussed herein, it will be appreciated that any suitable method may be used to generate forward and/or inverse whole-body motion fields.

At step 210, one or more forward and/or inverse whole-body motion fields are output for use in reconstruction of one or more diagnostic/clinical images from the acquired data set. For example, in some embodiments, each of the forward and inverse motion fields for each of the reconstructed image frames is output for use in an iterative parametric reconstruction process, as discussed in greater detail below. In other embodiments, a subset of the forward and/or inverse motion fields may be output for use in diagnostic image reconstruction.

Figure 5:
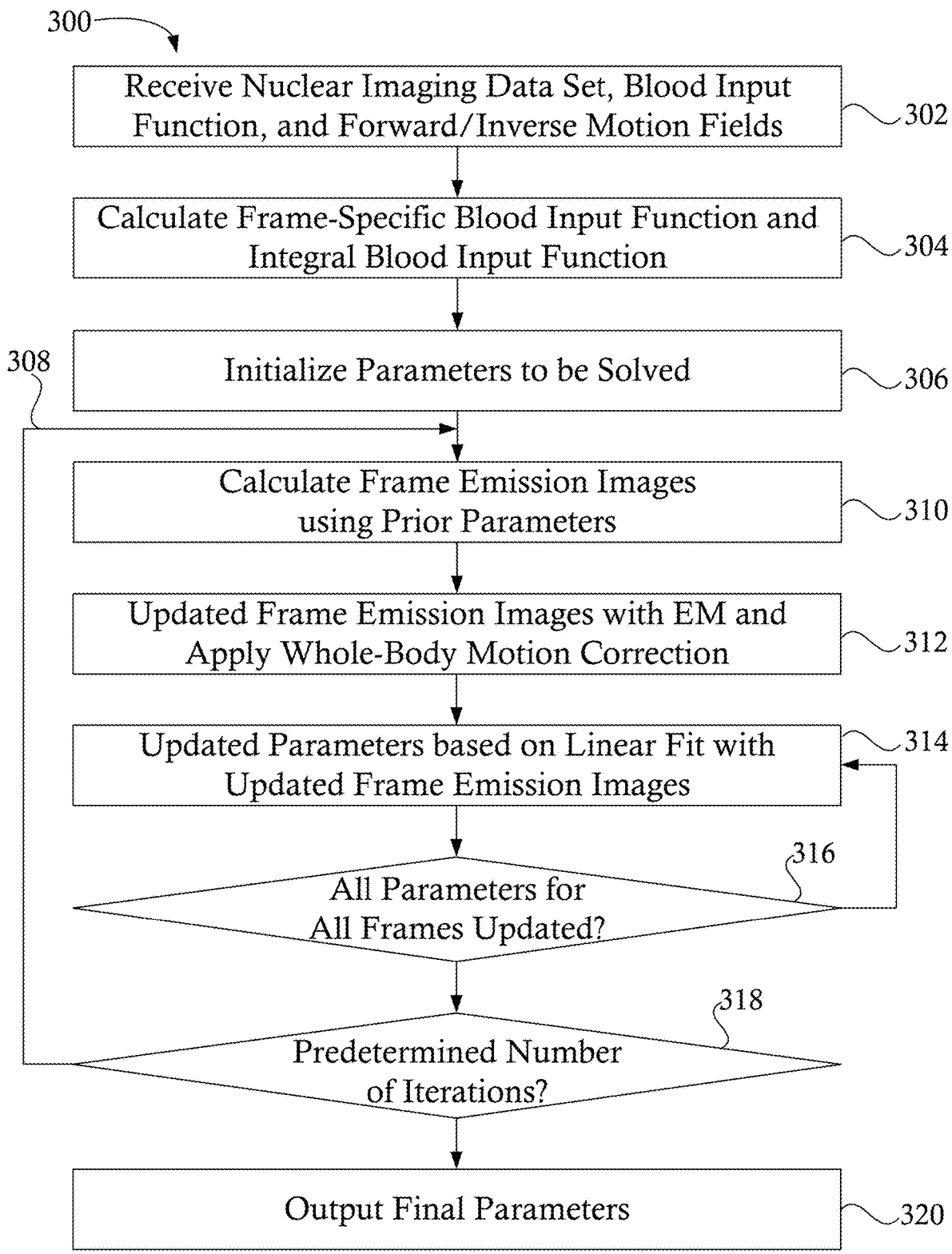
FIG. 5 is a flowchart illustrating a process of applying forward and inverse motion fields for motion correction, in accordance with some embodiments.
Figure 6:
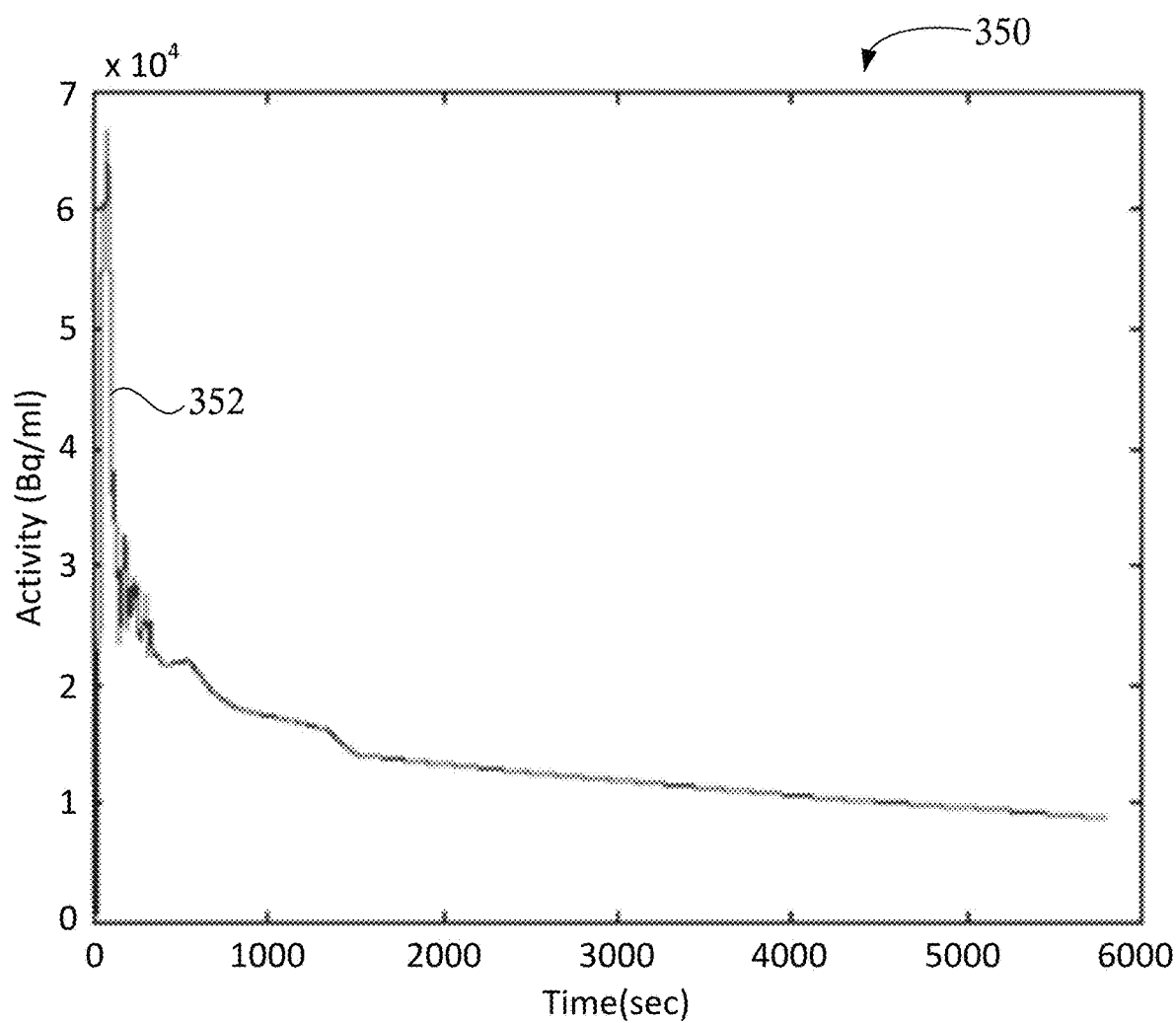
FIG. 6 is a graph illustrating a blood input function for generating parametric images, in accordance with some embodiments.

FIG. 5 is a flowchart 300 illustrating a process of parametric reconstruction using whole-body motion fields, in accordance with some embodiments. At step 302, the acquired data, a blood input function, and the forward/inverse motion fields (output at step 208 illustrated in FIG. 4) are provided as inputs. In some embodiments, the acquired data includes continuous bed motion sinograms obtained using one or more imaging modalities 12, 14, although it will be appreciated that any suitable acquired data, such as multi-bed or single-bed data, may be used. A blood input function includes an independent function representative of the concentration of a radiotracer in the patient's blood as a function of time. FIG. 6 is a graph 350 illustrating one embodiment a blood input function 352, although it will be appreciated that blood input functions may be dependent on one or more parameters, such as, for example, the radiotracer used for imaging, the scanner used for imaging, patient-specific parameters, etc.

At step 304, the blood input function, Cp(t) and an integral of the blood input function, ∫Cp(t) is calculated for each frame or axial slice in the acquired data. Each frame-specific blood input function, Cp(t), is represented as a curve over time. The frame-specific blood input function and integral may be calculated based on frame imaging time. In CBM scans, each axial slice has a unique imaging time. In a single bed scan, all axial slices can be assigned with the same imaging time.

At step 306, the parameters being solved in each parametric image are initialized, i.e., assigned an initial value. In some embodiments, the parameters of each parametric image may include, but are not limited to, 3D voxel space parameters such as metabolic uptake rate (Ki) and distribution volume (DV), although it will be appreciated that any suitable kinetic parameters for any suitable parametric model may be initialized, such as, for example, slope and intercept. Although embodiments are discussed herein using a Patlak equation including parameters Ki and DV, it will be appreciated that any suitable parametric reconstruction equation or process, with any suitable corresponding parameters, may be used.

An iterative loop 308 is applied to each voxel in an image independently. For each voxel, at step 310, a frame emission image is calculated using a predetermined equation based on the initialized parameters (or parameters from a prior iteration as discussed below), such as, for example, a Patlak equation using Ki and DV. In some embodiments, the target parameters, e.g., Ki and DV, are calculated based on the activity, x(t) at each voxel, where:

$$x(t) = K_i \cdot \int_0^t C_p(s)ds + DV \cdot c_p(t)$$

where DV and Ki are parameters in a voxel space and $C_p$ is the blood input function.

Figure 7:
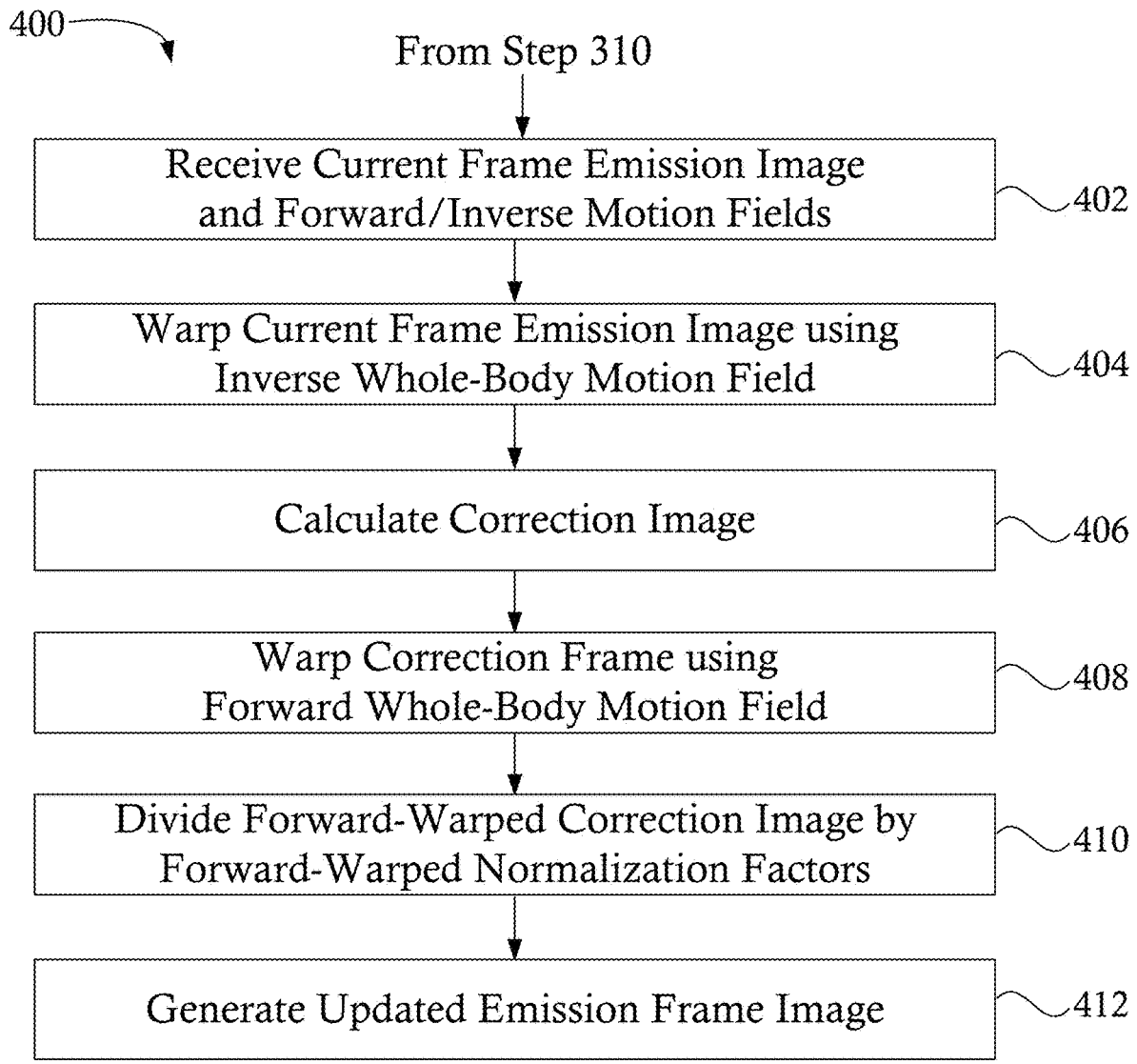
FIG. 7 is a flowchart illustrating a process of applying forward and inverse warping, in accordance with some embodiments.

At step 312, the frame emission images are updated using an expectation-maximization (EM) and motion correction using the whole-body motion filed. In some embodiments, updating the frame emission images includes warping each reconstructed frame image to and/or from a reference frame using the previously calculated whole-body motion frame. FIG. 7 is a flowchart illustrating a process 400 of updating frame emission images using whole-body motion fields, in accordance with some embodiments. The process 400 may be executed each time step 312 is executed in the iterative loop 308 of the process 300.

In some embodiments, at step 402, a current frame emission image, a forward whole-body motion field, and an inverse whole body motion field are received. The current frame emission image may be received from step 310 of process 300, retrieved from a storage device, and/or otherwise received. Similarly, the forward and inverse whole-body motion fields may be received from step 208 of process 200, retrieved from a storage device, and/or otherwise received.

At step 404, the inverse whole-body motion field corresponding to the current frame is applied to the current frame emission image to warp the current frame emission image from the reference frame to a float frame. At step 406, a correction image is calculated by back-projecting the ratio between measured sinogram data and forward projection of the warped image.

At step 408, the forward whole-body motion field corresponding to the current frame is applied to warp the correction image from the float frame to the reference frame to generate a forward-warped correction image. One embodiment of warping to and/or from the float frame based on forward/inverse motion fields is illustrated in FIG. 8. As illustrated in FIG. 8, in some embodiments, the forward and/or inverse motion field 450 includes an x component 452, a y component 454, and a z component 456 (i.e., the forward and/or inverse motion field 450 is a three-dimensional (3D) motion field). In some embodiments, forward and/or inverse motion warping (i.e., application of a forward and/or inverse whole-body motion field) may be performed based on tri-linear interpolation according to the equation:

$$M(f(x,y,z)) = \text{tri}(f(x+m_x, y+m_y, z+m_z))$$

where f is representative of the image (e.g., current frame emission image, correction image, etc.) prior to applying the motion warping, M is the motion field elements of the forward/inverse whole-body motion field $(m_x, m_y, m_z)$, and tri is a tri-linear interpolation.

Each voxel of each of the components 452-456 of the forward/inverse whole-body motion field 450 are applied to each voxel in an image to warp from a first frame 458 to a second frame 460. In the illustrated embodiment, the shade of each voxel indicates the distance that each voxel is warped from the first frame to the second frame. For example, in some embodiments, a forward whole-body motion field 450 is applied to warp (i.e., transform) each voxel of a float frame 458 to the corresponding voxel in a reference frame 460. Similarly, the inverse operation may be applied based on an inverse whole-body motion field 450 to warp each voxel of the reference frame 460 to the float frame 458.

At step 410, the forward-warped correction image (i.e., the voxel values of the forward-warped correction image) is divided by forward-warped normalization factors. The normalization factors may be scanner specific and may be determined using one or more iterative processes, such as, for example, by applying an iterative machine-learning process. In other embodiments, the forward-warped normalization factors may be known factors provided by, for example, the manufacturer of a scanner.

At step 412, an updated emission frame image is generated by applying the normalized forward-warped correction image to the current emission frame image. In the first iteration through the main loop 308, the current emission frame image is generated using the initialized parameter values. In each subsequent iteration through the main loop 308, the current emission frame image is the updated emission frame image generated during the prior iteration through the main loop 308. In some embodiments, activity reconstruction (e.g., updated emission frame image reconstruction) is performed according to the equation:

$$f^{i+1}(t) = f^i(t) \frac{1}{M_t\left(P^{-1}\left(\frac{1}{AN(t)}\right)\right)} M_t\left(P^{-1}\left(\frac{y(t)}{P(M_t^{-1}(f(t)) + r(t)) + s(t)}\right)\right)$$

where f is the current emission frame image, t is the index for dynamic frames, y is measured emission data, P is a forward projection, $P^1$ is an inverse (or back/reverse) projection, $M_t$, is a whole-body forward motion field for the frame t, $M_t^{-1}$ is the whole-body inverse motion field for the frame t, r is an expected value for randoms, s is an expected value for scatter, A is an attenuation correction factor, and N is a frame-dependent normalization factor.

With reference again to FIG. 5, at step 314, the image parameters, e.g., Ki, DV, slope, intercept, etc., are updated based on a linear/nonlinear fit of the updated emission frame images calculated at step 312. A linear/non-linear fit may be performed between each of the updated emission frame images, between each of the updated emission frame images and a reference image, and/or between any other suitable set of emission frame images. The linear/nonlinear fit can be an iterative process. At step 316, a check is performed to determine if the curve fit process has meet a certain criterion, for example, a predetermined number of iterations. If not, the process returns to step 314 for another iteration and updates the image parameters. If the parametric fit of emission frame images has met the pre-determined criteria, the process 300 proceeds to step 316.

At step 318, a check is performed to determine if a predetermined number of iterations of the main loop has been completed. If the predetermined number of iterations has not been reached, the main loop 308 repeats steps 310-316 using the set of updated emission frame images and updated parameters as input and further refining the parameters to be used in construction of the parametric images. It will be appreciated that the inclusion of whole-body motion correction using forward and inverse whole-body motion fields, such as forward/inverse whole-body motion field 450, during parametric reconstruction within the main loop 308 allows for the compensation and correction of small, rigid and non-rigid motion simultaneously. Further, the inclusion of the whole-body motion fields within the main loop 308 provides for improved signal-to-noise ratios as compared to applying motion correction as a post-filter.

If the predetermined number of iterations has been reached, the process 300 proceeds to step 320. At step 320, the calculated parameters for each parametric image, e.g., the Ki and DV image volumes, are output. The output parameters may be used to construct a set of parametric diagnostic images for use in diagnostic, treatment planning, and/or clinical activities. In some embodiments, the calculated parameters are stored in a non-transitory storage medium for later retrieval and construction of parametric images. The output parameters may be used to generated whole body parametric images in which motion artifacts are significantly reduced or eliminated compared to current parametric reconstructions. The compensated motion includes voluntary and involuntary bulk motion (e.g., head, arms, etc.), respirator motion, cardiac motion, etc.

Figure 10A:
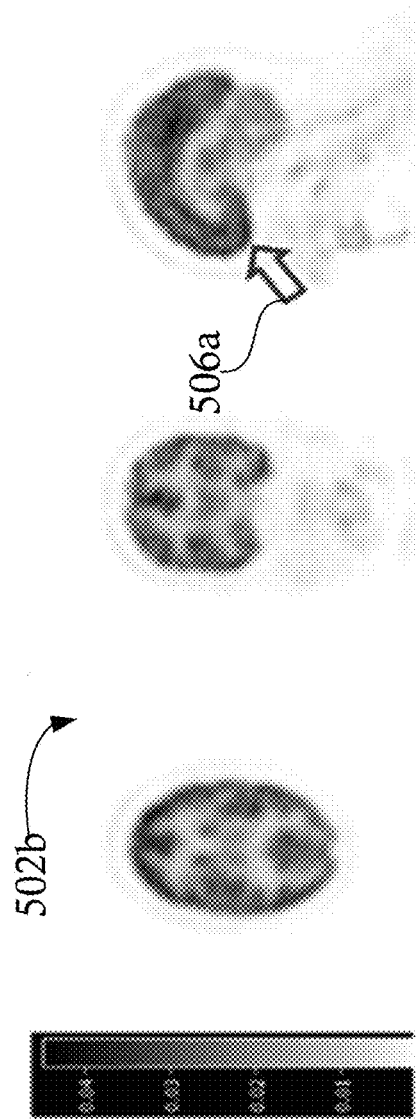
FIG. 10A illustrates a Ki brain parametric image reconstructed using a whole-body motion field parametric reconstruction process, in accordance with some embodiments.
Figure 10B:
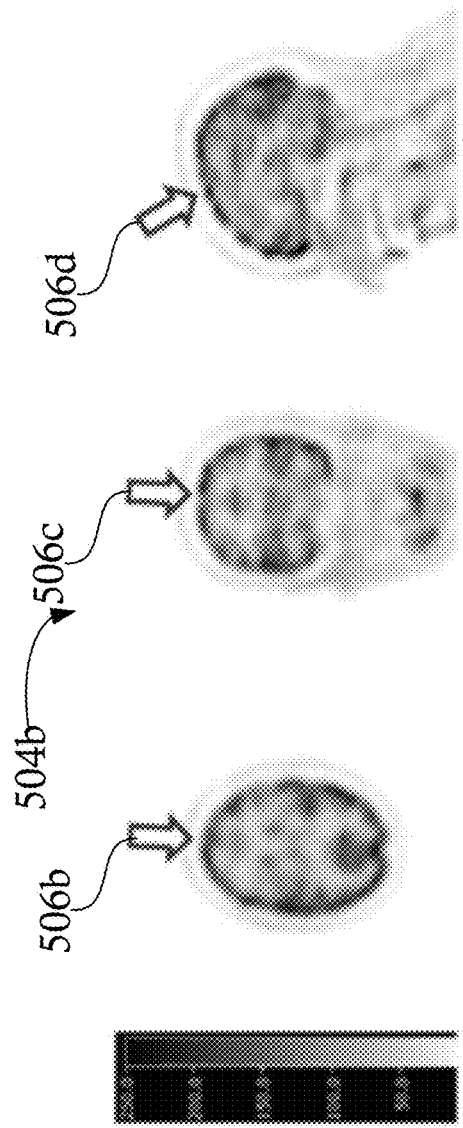
FIG. 10B illustrates a DV brain parametric image reconstructed using a whole-body motion field parametric reconstruction process, in accordance with some embodiments.

FIGS. 9A and 9B illustrate a set of brain parametric images 502a, 504a reconstructed without motion correction and FIGS. 10A and 10B illustrate a set of brain parametric images 502b, 504b reconstructed using a whole-body motion field parametric reconstruction process, such as the process illustrated in FIG. 5. As can be seen in FIGS. 9A-10B, the set of parametric images 502b, 504b generated using the whole-body motion field correction have fewer motion artifacts (as indicated by arrows 506a-506d). The post-motion corrected parametric images 502b, 504b have significantly better contrast and resolution and provide increased value as diagnostic and/or clinical images.

Figure 11B:
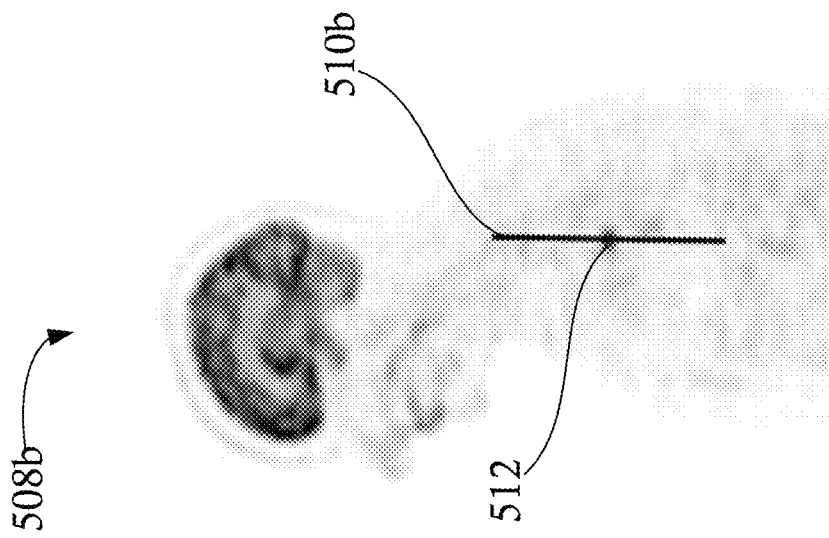
FIG. 11B illustrates an upper body parametric image reconstructed using a whole-body motion field parametric reconstruction process, in accordance with some embodiments.
Figure 11A:
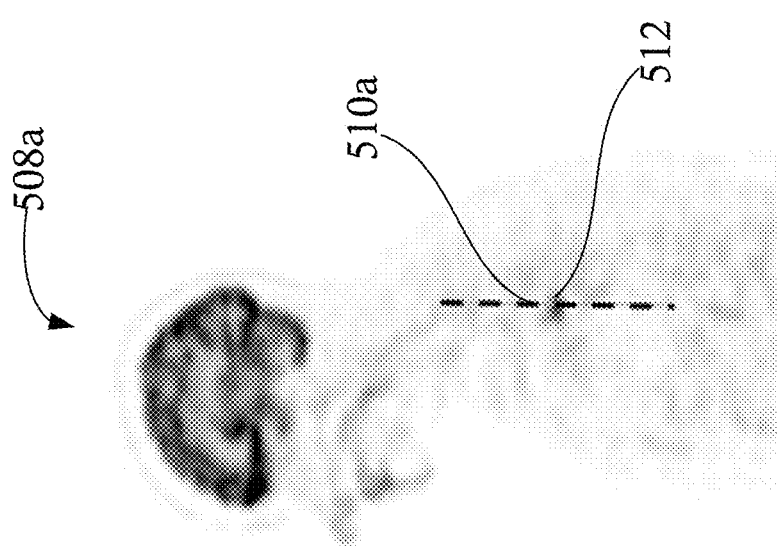
FIG. 11A illustrates an upper body parametric image reconstructed without applying motion correction.
Figure 11C:
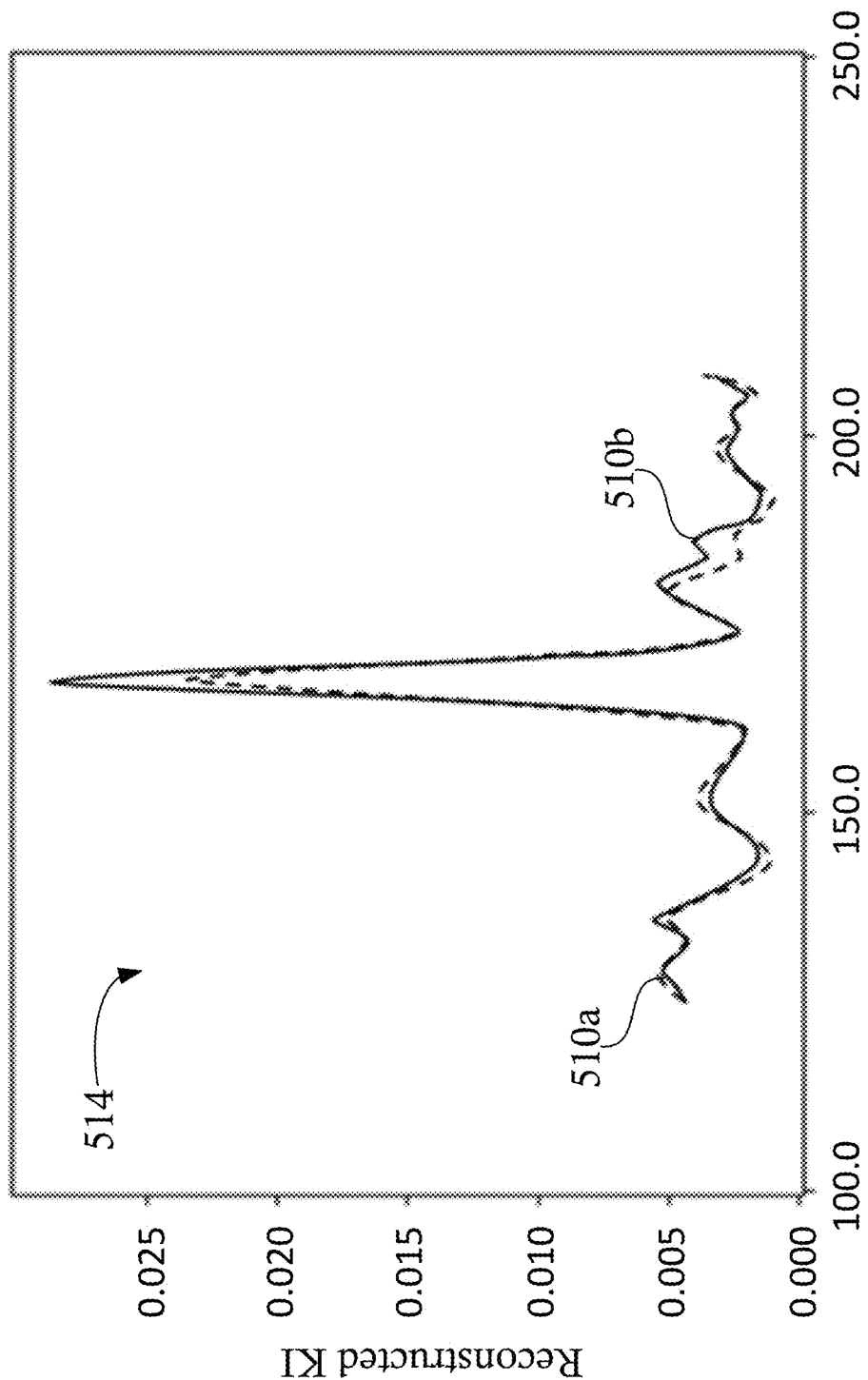
FIG. 11C is a graph illustrating line plots overlying a tumor in FIGS. 11A and 11B, in accordance with some embodiments.

FIG. 11A illustrates a metabolic uptake rate (Ki) sagittal image 508a reconstructed without motion correction and FIG. 11B illustrates a metabolic uptake rate (Ki) sagittal image 508b reconstructed using a whole-body motion field parametric reconstruction process, such as the process illustrated in FIG. 5. The motion-corrected sagittal image 508b has better contrast and resolution and provides increased diagnostic and/or clinical value as compared to the sagittal image 508a. For example, a line plot 510a, 510b is provided each sagittal image 508a, 508b corresponding to a tumor 512. As illustrated in the graph 514 of FIG. 11C, the line plot 510b in the motion-corrected sagittal image 508b has a higher correspondence to the tumor 512 as compared to the line plot 510a in the uncorrected sagittal image 508a. In the graph 514, the horizontal axis corresponds to a pixel index and the vertical axis corresponds to a Ki value.

Figures 12A, 12B:
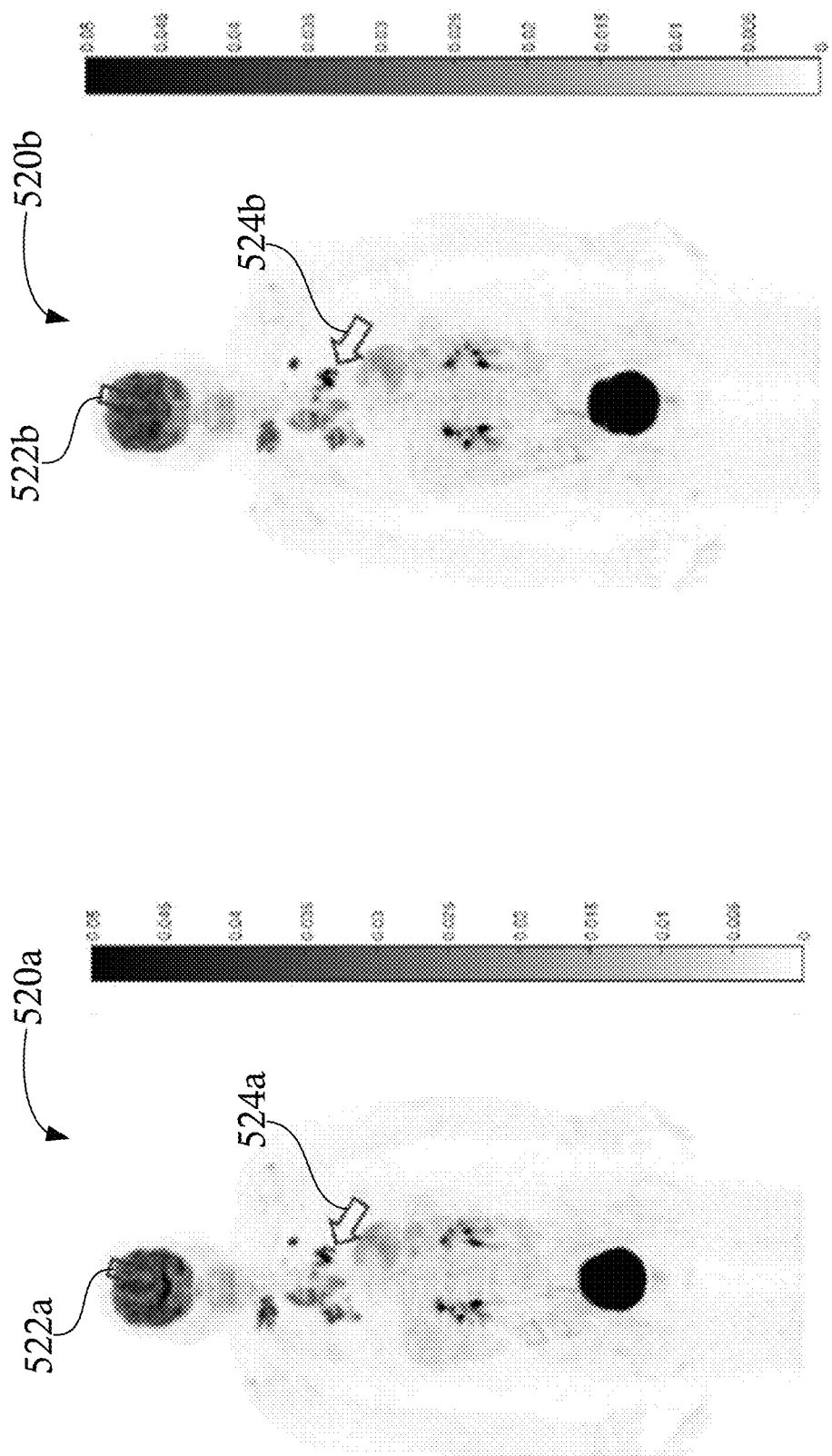
FIG. 12A illustrates a maximum intensity projection (MIP) metabolic uptake rate (Ki) image reconstructed without motion correction.
FIG. 12B illustrates a MIP Ki image reconstructed using a whole-body motion field parametric reconstruction process, in accordance with some embodiments.

FIG. 12A illustrates a whole-body maximum intensity projection (MIP) image 520a of a metabolic uptake rate (Ki) reconstructed without applying motion correction and FIG. 12B illustrates a whole-body MIP image 520b reconstructed using a whole-body motion field parametric reconstruction process, such as the process illustrated in FIG. 5. A first arrow 522a and a second arrow 524a indicate two motion artifacts in the uncorrected whole-body MIP image 520a that are removed, as indicated by arrows 522b, 524b, in the motion-corrected whole-body MIP image 520b.

Figure 13B:
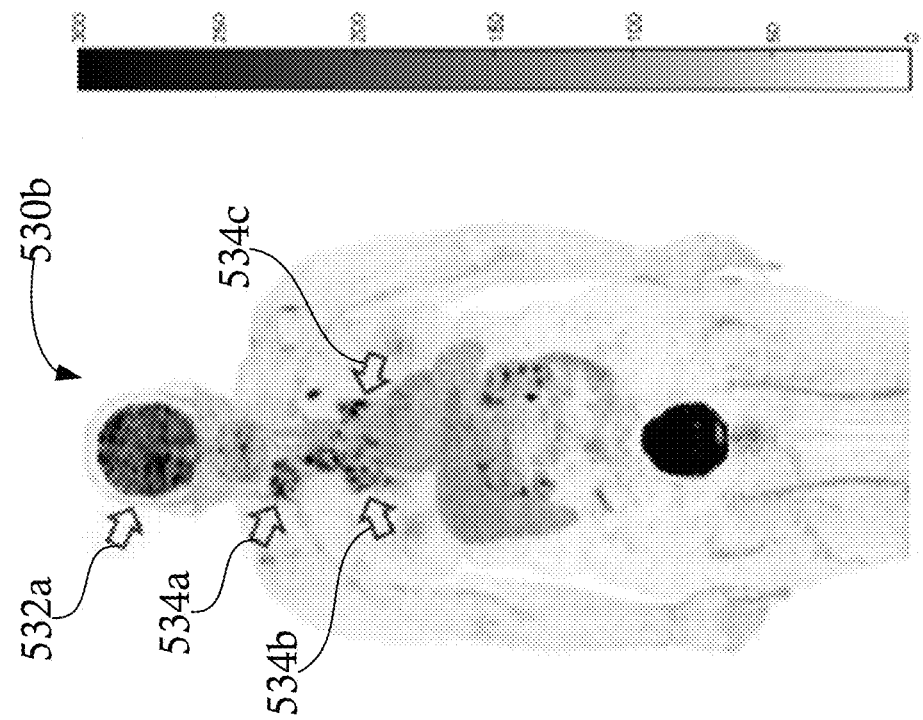
FIG. 13B illustrates a DV MIP image reconstructed using a whole-body motion field parametric reconstruction process, in accordance with some embodiments.
Figure 13A:
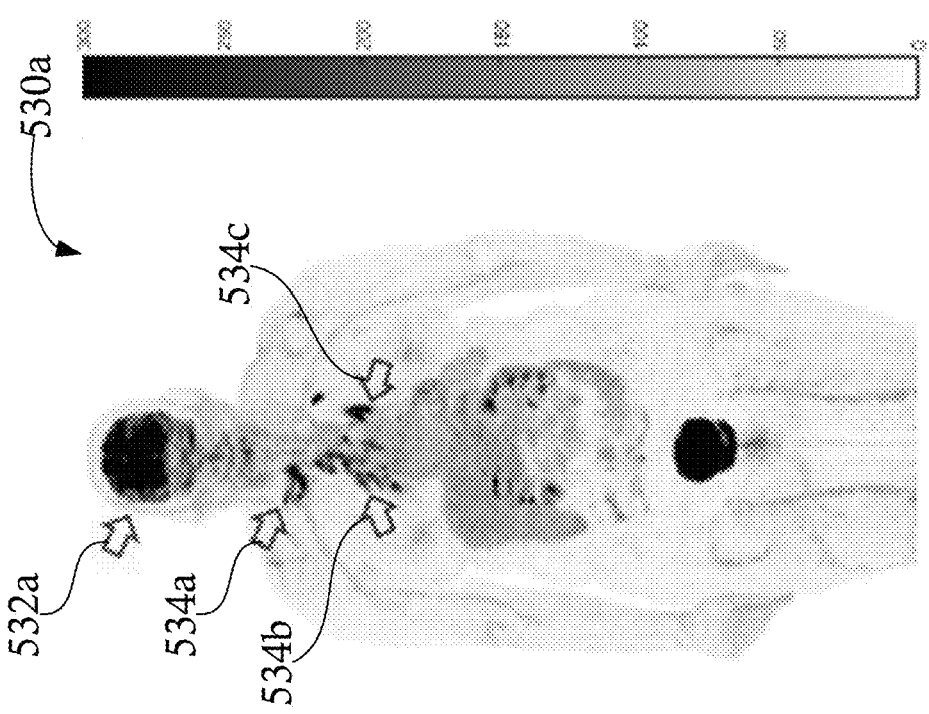
FIG. 13A illustrates a distribution volume (DV) MIP image reconstructed without motion correction.

FIG. 13A illustrates a DV MIP image 530a reconstructed without applying motion correction and FIG. 13B illustrates a DV MIP image 530b reconstructed using a whole-body motion field parametric reconstruction process, such as the process illustrated in FIG. 5. The uncorrected DV MIP image 530a includes a dark motion artifact 532a in the patient's brain. The artifact 532a is not present in the motion-corrected DV MIP image 530b, as indicated at 532b. In addition, although each of the DV MIP images 530a, 530b include hot spots 534a-534c, the hot spots 534a-534c in the motion-corrected DV MIP image 530b are better resolved, allowing more accurate targeting and diagnosis of the hot spots 534a-534c.

Figure 14B:
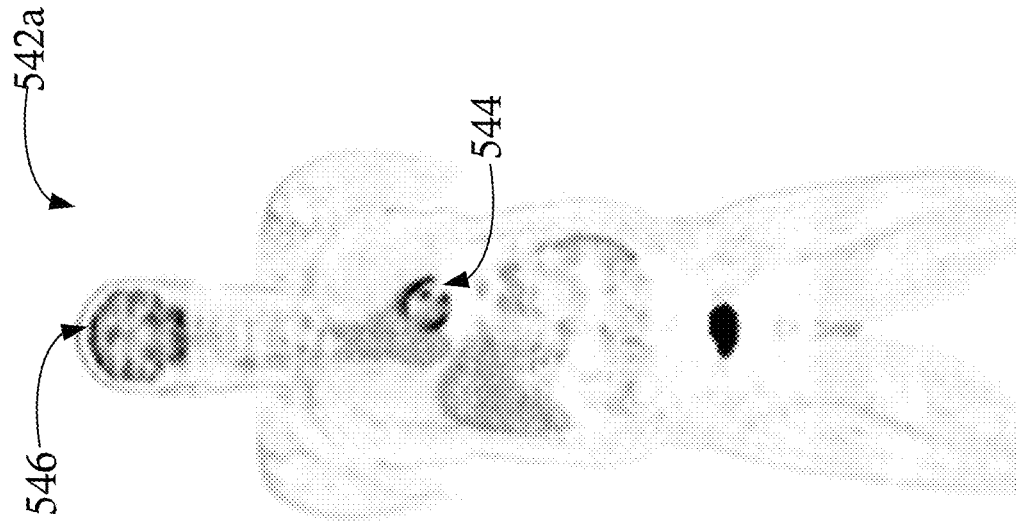
FIG. 14B illustrates a DV coronal parametric image reconstructed without motion correction.
Figure 14A:
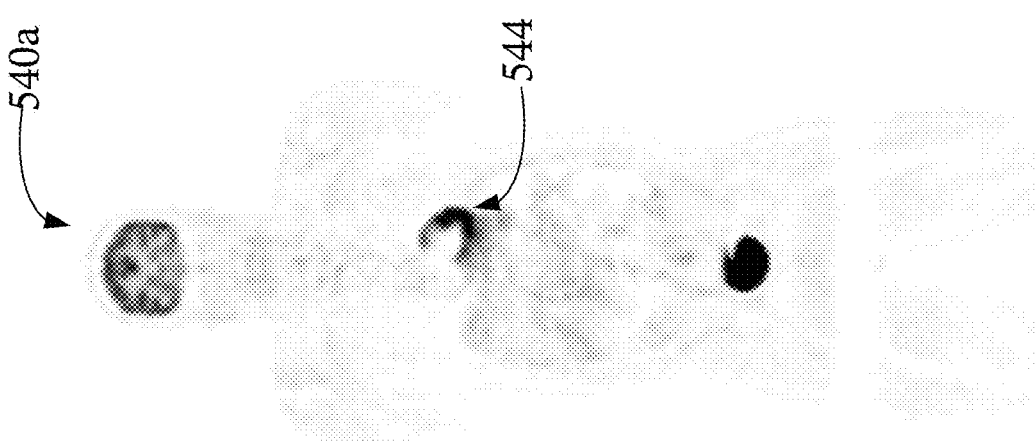
FIG. 14A illustrates a Ki coronal parametric image reconstructed without motion correction.
Figure 15B:
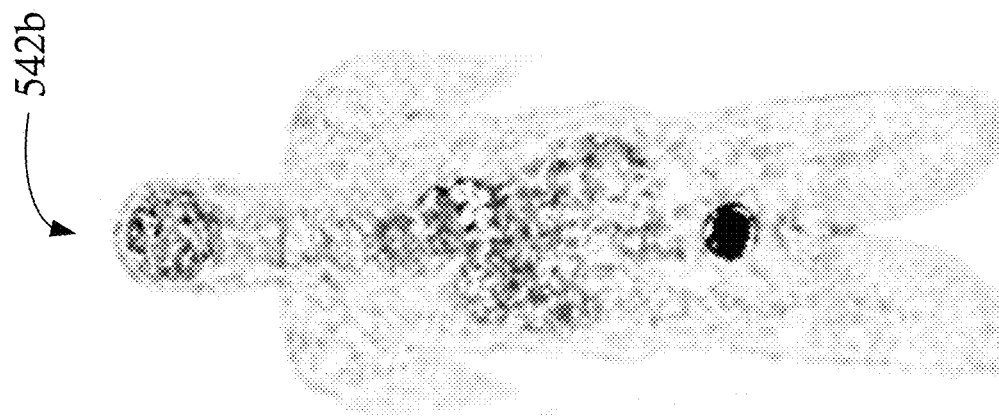
FIG. 15B illustrates a DV parametric whole-body image generated using an indirect parametric motion correction process.
Figure 15A:
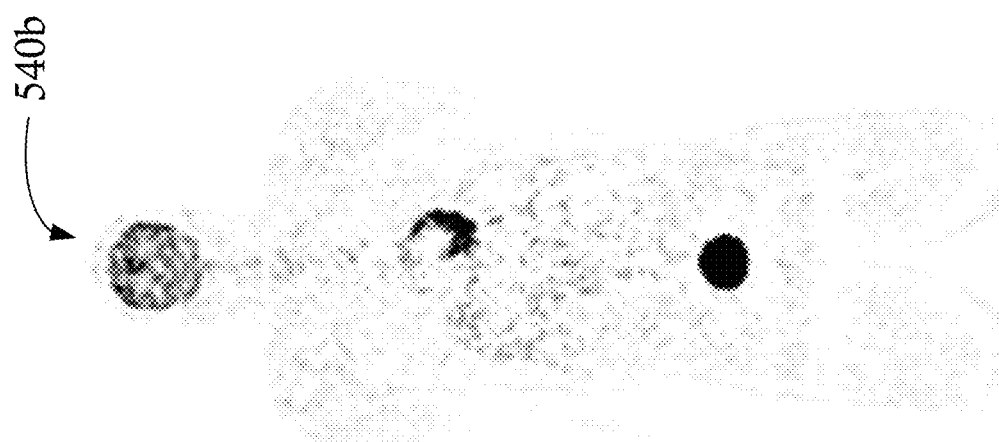
FIG. 15A illustrates a Ki parametric whole-body image generated using an indirect parametric motion correction process.
Figure 16B:
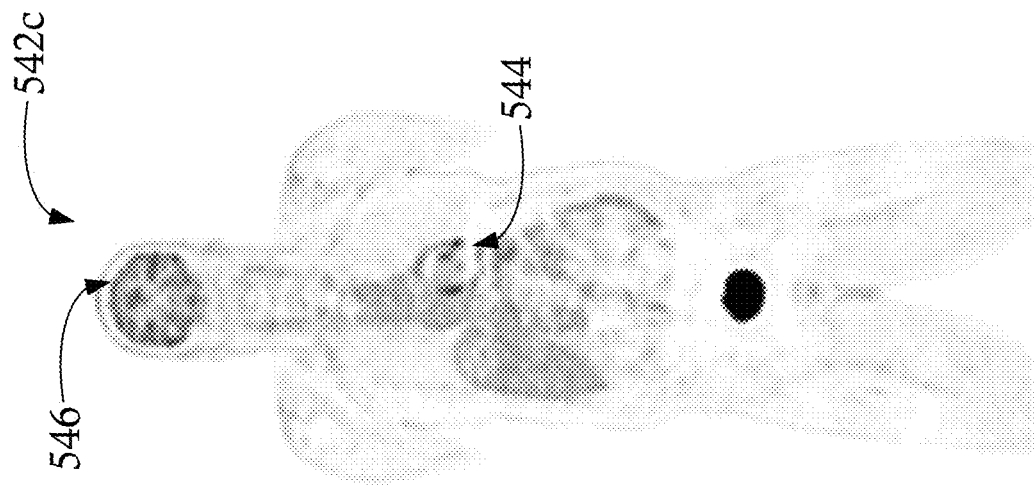
FIG. 16B illustrates a DV parametric whole-body image generated using the direct parametric reconstruction method of FIG. 5, in accordance with some embodiments.
Figure 16A:
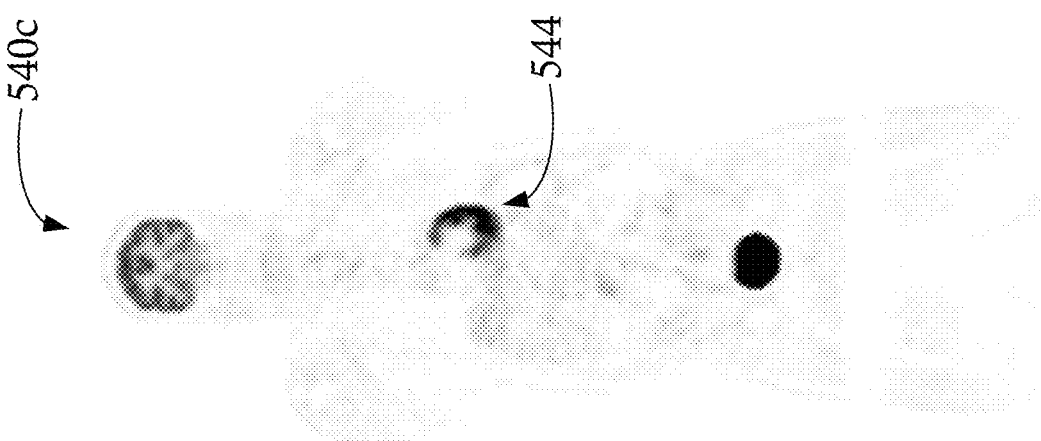
FIG. 16A illustrates a Ki parametric whole-body image generated using the direct parametric reconstruction method of FIG. 5, in accordance with some embodiments.

FIGS. 14A and 14B illustrate coronal parametric images 540a, 542a reconstructed without motion correction, FIGS. 15A and 15B illustrate motion corrected parametric images 540b, 542b reconstructed using an indirect parametric reconstruction, and FIGS. 16A and 16B illustrates motion corrected parametric images 540c, 542c reconstructed using a direct parametric reconstruction process including whole-body forward and inverse motion fields, such as the process illustrated in FIG. 5. The uncorrected coronal parametric images 540a, 542a include a motion artifact 544 (e.g., defect) in the heart and a motion artifact 546 in the brain. In contrast, in the motion-corrected parametric images 540c, 542c, the motion artifact 544 in the heart and the motion artifact 546 in the brain are each significantly reduced. Similarly, the direct parametric reconstruction 540c, 542c provides increased contrast, better resolved, and more accurate diagnostic and clinical images as compared to the indirect reconstructions 540b, 542b.

Although the subject matter has been described in terms of exemplary embodiments, it is not limited thereto. Rather, the appended claims should be construed broadly, to include other variants and embodiments, which may be made by those skilled in the art.

What is claimed is:

1. A computer-implemented method, comprising:
receiving a nuclear imaging data set including a set of dynamic frames;
generating at least one of a whole-body forward motion field or a whole-body inverse motion field for at least one frame in the set of dynamic frames;
applying an iterative loop to update at least one parameter used in a direct parametric reconstruction, wherein the iterative loop includes:
calculating frame emission images for the at least one frame;
generating motion-corrected frame emission images based on the at least one whole-body forward motion field or a whole-body inverse motion field; and
updating the at least one parameter by applying a linear or nonlinear fit to the motion-corrected frame emission images; and
generating at least one parametric image based on the at least one parameter updated by the iterative loop.

2. The computer-implemented method of claim 1, wherein generating at least one of a whole-body forward motion field or a whole-body inverse motion field for at least one frame in the set of frames comprises:
selecting a reference frame from the set of frames;
calculating the at least one of the whole-body forward motion field or the whole-body inverse motion field for each frame other than the reference frame in the set of frames; and
outputting the at least one of the whole-body forward motion field or the whole-body inverse motion field for each frame in the set of frames.

3. The computer-implemented method of claim 1, wherein calculating the motion-corrected frame emission image comprises applying an activity reconstruction.

4. The computer-implemented method of claim 3, wherein the activity reconstruction is performed according to:

$$f^{i+1}(t) = f^i(t) \frac{1}{M_t\left(P^{-1}\left(\frac{1}{AN(t)}\right)\right)} M_t\left(P^{-1}\left(\frac{y(t)}{P(M_t^{-1}(f(t)) + r(t)) + s(t)}\right)\right)$$

where f is the frame emission image, t is an index for a current frame in the set of frames, y is measured emission data, P is a forward projection, $P^{-1}$ is an inverse projection, $M_t$ is the whole-body forward motion field for the current frame t, $M_t^{-1}$ is the whole-body inverse motion field for the current frame t, r is an expected value for randoms, s is an expected value for scatter, A is an attenuation correction factor, and N is a frame-dependent normalization factor.

5. The computer-implemented method of claim 1, wherein the at least one of the whole-body forward motion field or the whole-body inverse motion field for the at least one frame in the set of frames according to:

$$M(f(x,y,z)) = \text{tri}(f(x+m_x, y+m_y, z+m_z))$$

where M is an application of one of the at least one of the whole-body forward motion field or the whole-body inverse motion field, f is the frame emission image of the at least one frame, $m_x$, $m_y$, $m_z$ are the motion field elements of the at least one whole-body forward motion field or the whole-body inverse motion field, and tri is a tri-linear interpolation.

6. The computer-implemented method of claim 1, wherein the at least one of a whole-body forward motion field or a whole-body inverse motion field for at least one frame in the set of frames is generated using a plurality of histo-images generated by a direct histogram of the nuclear imaging data set.

7. The computer-implemented method of claim 6, wherein the histo-images are filtered using a neural network trained using one or more ground-truth fully reconstructed images.

8. The computer-implemented method of claim 1, wherein the at least one parameter comprises a metabolic uptake rate (Ki) and a distribution volume (DV).

9. The computer-implemented method of claim 8, wherein direct parametric reconstruction comprises a direct Patlak reconstruction.

10. The computer-implemented method of claim 1, wherein the at least one parameter comprises a slope and an intercept.

11. The computer-implemented method of claim 1, wherein the nuclear imaging data set is selected from the group consisting of a PET imaging data set, a SPECT imaging data set, or a CT imaging data set.

12. The computer-implemented method of claim 1, wherein generating a motion-corrected frame emission image based on the at least one whole-body forward motion field or the whole-body inverse motion field comprises:
  applying the whole-body inverse motion field to the frame emission image;
  calculating a correction image; and
  applying the whole-body forward motion field to the correction image.

13. The computer-implemented method of claim 12, wherein generating a motion-corrected frame emission image based on the at least one whole-body forward motion field or the whole-body inverse motion field further comprises dividing correction image by at least one forward warped normalization factor.

14. A system, comprising:
  a nuclear imaging scanner configured to obtain a set of nuclear imaging data including a set of frames; and
  a processor configured to:
    receive the nuclear imaging data set from the nuclear imaging scanner;
    generate at least one of a whole-body forward motion field or a whole-body inverse motion field for at least one frame in the set of frames;
    apply an iterative loop to update at least one parameter used in a direct parametric reconstruction, wherein the iterative loop includes:
      calculating a frame emission image for the at least one frame;
      generating a motion-corrected frame emission image based on the at least one whole-body forward motion field or a whole-body inverse motion field; and
      updating the at least one parameter by applying a linear or nonlinear fit to the motion-corrected frame emission image; and
    generate at least one parametric image based on the at least one parameter updated by the iterative loop.

15. The system of claim 14, wherein the motion-corrected frame emission image is calculated by applying a parametric activity reconstruction according to:

$$f^{i+1}(t) = f^i(t) \frac{1}{M_t\left(P^{-1}\left(\frac{1}{AN(t)}\right)\right)} M_t\left(P^{-1}\left(\frac{y(t)}{P(M_t^{-1}(f(t)) + r(t)) + s(t)}\right)\right)$$

where f is the frame emission image, t is an index for a current frame in the set of frames, y is measured emission data, P is a forward projection, $P^{-1}$ is an inverse projection, $M_t$ is the whole-body forward motion field for the current frame t, $M_t^{-1}$ is the whole-body inverse motion field for the current frame t, r is an expected value for randoms, s is an expected value for scatter, A is an attenuation correction factor, and N is a frame-dependent normalization factor.

16. The system of claim 14, wherein the at least the whole-body forward motion field or the whole-body inverse motion field for the at least one frame in the set of frames according to:

$$M(f(x,y,z)) = \text{tri}(f(x+m_x, y+m_y, z+m_z))$$

where M is an application of one of the at least one of the whole-body forward motion field or the whole-body inverse motion field, f is the frame emission image of the at least one frame, $m_x$, $m_y$, $m_z$ are the motion field elements of the at least one whole-body forward motion field or the whole-body inverse motion field, and tri is a tri-linear interpolation.

17. The system of claim 14, wherein the at least one parameter comprises a metabolic uptake rate (Ki) and a distribution volume (DV).

18. The non-transitory computer readable medium of claim 17, wherein the at least the whole-body forward motion field or the whole-body inverse motion field for the at least one frame in the set of frames according to:

$$M(f(x,y,z)) = \text{tri}(f(x+m_x, y+m_y, z+m_z))$$

where M is an application of one of the at least one of the whole-body forward motion field or the whole-body inverse motion field, f is the frame emission image of the at least one frame, $m_x$, $m_y$, $m_z$ are the motion field elements of the at least one whole-body forward motion field or the whole-body inverse motion field, and tri is a tri-linear interpolation.

19. A non-transitory computer readable medium storing instructions configured to cause a computer system to execute the steps of:
  receiving a nuclear imaging data set including a set of frames;
  generating at least one of a whole-body forward motion field or a whole-body inverse motion field for at least one frame in the set of frames;
  applying an iterative loop to update at least one parameter used in a direct parametric reconstruction, wherein the iterative loop includes:
    calculating a frame emission image for the at least one frame;
    generating a motion-corrected frame emission image based on the at least one whole-body forward motion field or a whole-body inverse motion field; and
    updating the at least one parameter by applying a linear fit to the motion-corrected frame emission image; and
  generating at least one parametric image based on the at least one parameter updated by the iterative loop.

20. The non-transitory computer readable medium of claim 19, wherein calculating the motion-corrected frame emission image comprises applying a parametric activity reconstruction according to:

$$f^{i+1}(t) = f^i(t) \frac{1}{M_t\left(P^{-1}\left(\frac{1}{AN(t)}\right)\right)} M_t\left(P^{-1}\left(\frac{y(t)}{P(M_t^{-1}(f(t)) + r(t)) + s(t)}\right)\right)$$

where f is the frame emission image, t is an index for a current frame in the set of frames, y is measured emission data, P is a forward projection, $P^{-1}$ is an inverse projection, $M_t$ is the whole-body forward motion field for the current frame t, $M_t^{-1}$ is the whole-body inverse motion field for the current frame t, r is an expected value for randoms, s is an expected value for scatter, A is an attenuation correction factor, and N is a frame-dependent normalization factor.

* * * * *